(12) United States Patent
Pevarello et al.

(10) Patent No.: US 6,863,647 B2
(45) Date of Patent: Mar. 8, 2005

(54) 2-UREIDO-THIAZOLE DERIVATIVES, PROCESS FOR THEIR PREPARATION, AND THEIR USE AS ANTITUMOR AGENTS

(75) Inventors: Paolo Pevarello, Pavia (IT); Raffaella Amici, Piacenza (IT); Gabriella Traquandi, Milan (IT); Manuela Villa, Lurago d' Erba (IT); Anna Vulpetti, Brugherio (IT); Antonella Isacchi, Milan (IT)

(73) Assignee: Pharmacia & Upjohn S.p.A., Milan (IT)

( * ) Notice: Subject to any disclaimer, the term of this patent is extended or adjusted under 35 U.S.C. 154(b) by 0 days.

(21) Appl. No.: 09/830,668

(22) PCT Filed: Oct. 27, 1999

(86) PCT No.: PCT/EP99/08307

§ 371 (c)(1),
(2), (4) Date: Apr. 30, 2001

(87) PCT Pub. No.: WO00/26203

PCT Pub. Date: May 11, 2000

(65) Prior Publication Data

US 2003/0187040 A1 Oct. 2, 2003

(30) Foreign Application Priority Data

Oct. 30, 1998 (GB) .............................................. 9823873

(51) Int. Cl.⁷ ............................................. C07D 877/48
(52) U.S. Cl. ..................................................... 598/196
(58) Field of Search .......................... 548/196; 514/371

(56) References Cited

U.S. PATENT DOCUMENTS 6,187,799 B1 * 2/2001 Wood et al. ................ 514/363

FOREIGN PATENT DOCUMENTS

| HU | 168393 B | 11/1973 |
| HU | 209839 B | 4/1989 |
| WO | WO 97/40028 A1 | 10/1997 |

* cited by examiner

*Primary Examiner*—Robert Gerstl
(74) *Attorney, Agent, or Firm*—Scully, Scott, Murphy & Presser

(57) ABSTRACT

Compounds which are 2-ureido-1,3-thiazole derivatives of formula (I) wherein R is a halogen atom, a nitro group, an optionally substituted amino group or it is a group optionally further substituted, selected from: i) straight or branched $C_1$–$C_6$ alkyl; ii) $C_3$–$C_6$ cycloalkyl; iii) aryl or arylalkyl with from 1 to 6 carbon atoms within the straight or branched alkyl chain; $R_1$ is an optionally substituted group selected from: i) straight or branched $C_1$–$C_6$ alkyl; ii) 3 to 6 membered carbocycle or 5 to 7 membered heterocycle ring; iii) aryl or arylcarbonyl; iv) arylalkyl with from 1 to 6 carbon atoms within the straight or branched alkyl chain; $R_2$ is hydrogen, a straight or branched $C_1$–$C_6$ alkyl or $C_2$–$C_4$ alkenyl or alkynyl group; or, taken together with the nitrogen atom so which they are bonded, $R_1$ and $R_2$ form a substituted or unsubstituted group selected from: i) an optionally benzocondensed or bridged 5 to 7 membered heterocycle; or ii) a 9 to 11 membered spiro-heterocyclic compound; or a pharmaceutically acceptable salt thereof; are useful for treating cell proliferative disorders associated with an altered cell dependent kinase activity.

3 Claims, No Drawings

2-UREIDO-THIAZOLE DERIVATIVES, PROCESS FOR THEIR PREPARATION, AND THEIR USE AS ANTITUMOR AGENTS

The present invention relates to 2-ureido-thiazole derivatives and, more in particular, it relates to 2-ureido-1,3-thiazoles, to a process for their preparation, to pharmaceutical compositions containing them and to their use as therapeutic agents, particularly in the treatment of cancer and cell proliferative disorders.

Several cytotoxic drugs such as, e.g. fluorouracil (5-FU), doxorubicin and camptothecins result to damage DNA or to affect cellular metabolic pathways and thus cause, in many cases, an indirect block of the cell cycle.

Therefore, by producing an irreversible damage to both normal and tumor cells, these agents result in a significant toxicity and side-effects.

In this respect, compounds capable of being highly specific antitumor agents by selectively leading to tumor cell arrest and apoptosis, with comparable efficacy but reduced toxicity than the currently available drugs, are desirable.

It is well known in the art that progression through the cell cycle is governed by a series of checkpoint controls, otherwise referred to as restriction points, which are regulated by a family of enzymes known as the cyclin-dependent kinases (cdk).

In their turn, the cdks themselves are regulated at many levels such as, for instance, binding to cyclins.

A normal progression through the cell cycle is controlled by the coordinated activation and inactivation of different cyclin/cdk complexes. In G1, both cyclin D/cdk4 and cyclin E/cdk2 are thought to mediate the onset of S-phase. Progression through S-phase requires the activity of cyclin A/cdk2 whereas the activation of cyclin A/cdc2 (cdk1) and cyclin B/cdc2 are required for the onset of metaphases.

For a general reference to cyclins and cyclin-dependent kinases see, for instance, Kevin R. Webster et al. in Exp. Opin. Invest. Drugs, 1998, Vol. 7(6), 865–887.

Checkpoint controls are defective in tumor cells due, in part, to disregulation of cdk activity. For example, altered expression of cyclin E and cdk's has been observed in tumor cells, and deletion of the cdk inhibitor p27 KIP gene in mice has been shown to result in a higher incidence of cancer.

Increasing evidence supports the idea that the cdks are rate-limiting enzymes in cell cycle progression and, as such, represent molecular targets for therapeutic intervention. In particular, the direct inhibition of cdk/cyclin kinase activity should be helpful in restricting the unregulated proliferation of a tumor cell.

It has now been found that the 2-ureido-1,3-thiazoles of the invention are endowed with cdk/cyclin kinase inhibitory activity and are thus useful in therapy as antitumor agents whilst lacking, in terms of both toxicity and side effects, the aforementioned drawbacks known for currently available antitumor drugs.

More specifically, the compounds of this invention are useful in the treatment of a variety of cancers including, but not limited to: carcinoma such as bladder, breast, colon, kidney, liver, lung, including small cell lung cancer, esophagus, gall-bladder, ovary, pancreas, stomach, cervix, thyroid, prostate, and skin, including squamous cell carcinoma; hematopoietic tumors of lymphoid lineage, including leukemia, acute lymphocitic leukemia, acute lymphoblastic leukemia, B-cell lymphoma, T-cell-lymphoma, Hodgkin's lymphoma, non-Hodgkin's lymphoma, hairy cell lymphoma and Burkett's lymphoma; hematopoietic tumors of myeloid lineage, including acute and chronic myelogenous leukemias, myelodysplastic syndrome and promyelocytic leukemia; tumors of mesenchymal origin, including fibrosarcoma and rhabdomyosarcoma; tumors of the central and peripheral nervous system, including astrocytoma, neuroblastoma, glioma and schwannomas; other tumors, including melanoma, seminoma, teratocarcinoma, osteosarcoma, xenoderoma pigmentosum, keratoctanthoma, thyroid follicular cancer and Kaposi's sarcoma.

Due to the key role of cdks in the regulation of cellular proliferation, these 2-ureido-1,3-thiazole derivatives are also useful in the treatment of a variety of cell proliferative disorders such as, for instance, benign prostate hyperplasia, familial adenomatosis, polyposis, neuro-fibromatosis, psoriasis, vascular smooth cell proliferation associated with atherosclerosis, pulmonary fibrosis, arthritis, glomerulonephritis and post-surgical stenosis and restenosis.

The compounds of the invention can be useful in the treatment of Alzheimer's disease, as suggested by the fact that cdk5 is involved in the phosphorylation of tau protein (J. Biochem., 117, 741–749, 1995).

The compounds of this invention, as modulators of apoptosis, could be useful in the treatment of cancer, viral infections, prevention of AIDS development in HIV-infected individuals autoimmune diseases and neurodegenerative disorder.

The compounds of this invention could be useful in inhibiting tumor angiogenesis and metastasis.

The compounds of this invention may also act as inhibitors of other protein kinases, e.g. protein kinase C, her2, raf1, MEK1, MAP kinase, EGF receptor, PDGF receptor, IGF receptor, PI3 kinase, weel kinase, Src, Ab1 and thus be effective in the treatment of diseases associated with other protein kinases.

Several 2-ureido-1,3-thiazole derivatives are known in the art, particularly as herbicides or as synthetic intermediates for preparing herbicides [see, for a general reference, U.S. Pat. No. 3,726,891 in the name of Shell Co., and C.A. 83(1975):114381].

Just few examples among them are N'methyl- and N'-ehtyl-N-(5-bromo-2-thiazolyl)-urea; N'-methyl-, N'-ethyl- or N'-phenyl-N-(5-chloro-2-thiazolyl)-urea; N-(5-chloro-2-thiazolyl)-N',N'-dimethyl-urea; N-(5-bromo-2-thiazolyl)-N',N'-dimethyl-urea; N'-methyl- and N'-phenyl-N-(5-methyl-2-thiazolyl)-urea.

Other 2-ureido-1,3-thiazole derivatives have been described in the art as therapeutic agents.

Among them are N-methyl- and N-phenyl-N'-(5-chloro-2-thiazolyl)-urea which have been described as sedative and antiinflammatory agents in FR M. 7428 (Melle-bezons) or N-[4-(5-oxazolyl)phenyl]-N'-(5-methyl-2-thiazolyl) described as inosine 5'-monophosphate dehydrogenase inhibitor (IMPDH) in WO 97/40028 (Vertex Pharmaceuticals Inc.).

Accordingly, the present invention provides the use of a compound which is a 2-ureido-1,3-thiazole derivatives of formula (I)

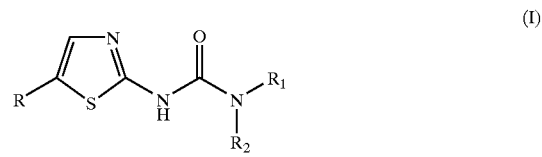

wherein
R is a halogen atom, a nitro group, an optionally substituted amino group or it is a group, optionally further substituted, selected from:
  i) straight or branched $C_1$–$C_6$ alkyl;
  ii) $C_3$–$C_6$ cycloalkyl;
  iii) aryl or arylalkyl with from 1 to 6 carbon atoms within the straight or branched alkyl chain;
$R_1$ is an optionally further substituted group selected from:

i) straight or branched $C_1$–$C_6$ alkyl;
ii) 3 to 6 membered carbocycle or 5 to 7 membered heterocycle ring;
iii) aryl or arylcarbonyl;
iv) arylalkyl with from 1 to 6 carbon atoms within the straight or branched alkyl chain;

$R_2$ is hydrogen, a straight or branched $C_1$–$C_4$ alkyl or $C_2$–$C_4$ alkenyl or alkynyl group; or, taken together with the nitrogen atom to which they are bonded, $R_1$ and $R_2$ form a substituted or unsubstituted group selected from:
  i) an optionally benzocondensed or bridged 5 to 7 membered heterocycle; or
  ii) a 9 to 11 membered spiro-heterocyclic compound;

or a pharmaceutically acceptable salt thereof; in the manufacture of a medicament for treating cell proliferative disorders associated with an altered cell dependent kinase activity.

According to a preferred embodiment of the invention, the said cell proliferative disorder is selected from the group consisting of cancer, Alzheimer's disease, viral infections, autoimmune diseases or neurodegenerative disorders.

Preferably, the cancer is selected from the group consisting of carcinoma, squamous cell carcinoma, hematopoietic tumors of myeloid or lymphoid lineage, tumors of mesenchymal origin, tumors of the central and peripheral nervous system, melanoma, seminoma, teratocarcinoma, osteosarcoma, xenoderoma pigmentosum, keratoctanthoma, thyroid follicular cancer and Kaposi's sarcoma.

According to another preferred embodiment of the invention, the cell proliferative disorder is selected from the group consisting of benign prostate hyperplasia, familial adenomatosis polyposis, neuro-fibromatosis, psoriasis, vascular smooth cell proliferation associated with atherosclerosis, pulmonary fibrosis, arthritis glomerulonephritis and post-surgical stenosis and restenosis.

In addition, being useful in the treatment of cell proliferative disorders associated with an altered cell dependent kinase activity, hence cell cycle inhibition or cdk/cyclin dependent inhibition, the compounds of formula (I) of the invention also enable tumor angiogenesis and metastasis inhibition.

As above reported, some of the compounds of formula (I) of the invention have been reported in the art as useful therapeutic agents, for instance as antiinflammatory, sedative and analgesic agents.

Therefore, it is a further object of the present invention a compound which is a 2-ureido-1,3-thiazole derivative of formula (I)

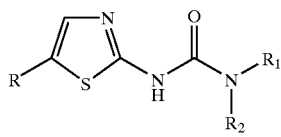

(I)

wherein

R is a halogen atom, a nitro group, an optionally substituted amino group or it is a group, optionally further substituted, selected from:
  i) straight or branched $C_1$–$C_6$ alkyl;
  ii) $C_3$–$C_6$ cycloalkyl;
  iii) aryl or arylalkyl with from 1 to 6 carbon atoms within the straight or branched alkyl chain;

$R_1$ is an optionally further substituted group selected from:
  i) straight or branched $C_1$–$C_6$ alkyl;
  ii) 3 to 6 membered carbocycle or 5 to 7 membered heterocycle ring;
  iii) aryl or arylcarbonyl;
  iv) arylalkyl with from 1 to 6 carbon atoms within the straight or branched alkyl chain;

$R_2$ is hydrogen, a straight or branched $C_1$–$C_4$ alkyl or $C_2$–$C_4$ alkenyl or alkynyl group; or, taken together with the nitrogen atom to which they are bonded, $R_1$ and $R_2$ form a substituted or unsubstituted group selected from:
  i) an optionally benzocondensed or bridged 5 to 7 membered heterocycle; or
  ii) a 9 to 11 membered spiro-heterocyclic compound; or a pharmaceutically acceptable salt thereof; for use as a inedicament; provided that:
    a) when R is a chlorine atom and $R_2$ is hydrogen, then $R_1$ is not methyl, phenyl or trifluoromethylphenyl; and
    b) when R is methyl and $R_2$ is hydrogen, then $R_1$ is not 4-(5-oxazolyl)phenyl.

Among the compounds of formula (I) above reported, several derivatives result to be novel.

Therefore, the present invention further provides a compound which is a 2-amino-1,3-thiazole derivative of formula (I)

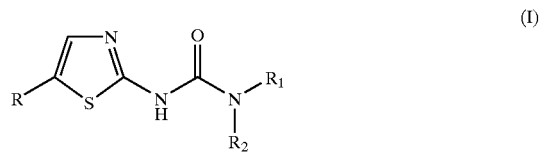

(I)

wherein

R is a halogen atom, a nitro group, an optionally substituted amino group or it is a group, optionally further substituted, selected from:
  i) straight or branched $C_1$–$C_6$ alkyl;
  iii) $C_3$–$C_6$ cycloalkyl;
  iv) aryl or arylalkyl with from 1 to 6 carbon atoms within the straight or branched alkyl chain;

$R_1$ is an optionally further substituted group selected from:
  i) straight or branched $C_1$–$C_6$ alkyl;
  ii) 3 to 6 membered carbocycle or 5 to 7 membered heterocycle ring;
  iii) aryl or arylcarbonyl;
  iv) arylalkyl with from 1 to 6 carbon atoms within the straight or branched alkyl chain;

$R_2$ is hydrogen, a straight or branched $C_1$–$C_4$ alkyl or $C_2$–$C_4$ alkenyl or alkynyl group; or, taken together with the nitrogen atom to which they are bonded, $R_1$ and $R_2$ form a substituted or unsubstituted group selected from:
  i) an optionally benzocondensed or bridged 5 to 7 membered heterocycle; or
  ii) a 9 to 11 membered spiro-heterocyclic compound; or a pharmaceutically acceptable salt thereof; provided that:
    a) when R is chlorine or bromine and $R_2$ is hydrogen, then $R_1$ is not unsubstituted $C_1$–$C_3$ alkyl, phenyl, trifluoromethylphenyl or an optionally substituted phenylcarbonyl;
    b) when R is methyl and $R_2$ is hydrogen, then $R_1$ is not methyl, phenyl or 4-(5-oxazolyl)phenyl;
    c) when R is nitrophenyl and $R_2$ is hydrogen, then $R_1$ is not haloalkyl;

d) when R is bromine or chlorine, then $R_1$ and $R_2$ are not both methyl groups.

The compounds of formula (I) may have asymmetric carbon atoms and may therefore exist either as racemic admixtures or as individual optical isomers.

Accordingly, all the possible isomers and their admixtures and of both the metabolites and the pharmaceutically acceptable bio-precursors (otherwise referred to as pro-drugs) of the compounds of formula (I), as well as the uses thereof, are also within the scope of the present invention.

In the present description, unless otherwise specified, with the term halogen atom we intend a chlorine, bromine, fluorine or iodine atom With the term optionally substituted amino group we intend an amino group wherein one or both hydrogen atoms are optionally replaced by other substituents which are the same or different, as set forth below.

With the term straight or branched $C_1$–$C_6$ alkyl we intend a group such as, for instance, methyl, ethyl, n.propyl, isopropyl, n.butyl, isobutyl, sec-butyl, tert-butyl, n.pentyl, n.hexyl and the like.

With the term straight or branched $C_2$–$C_4$ alkenyl or alkynyl group we intend a group such as, for instance, vinyl, allyl, isopropenyl, 1-, 2- or 3-butenyl, isobutylenyl, ethynyl, 1- or 2-propynyl, butynyl and the like.

With the term $C_3$–$C_6$ cycloalkyl we intend a cyclopropyl, cyclobutyl, cyclopentyl or cyclohexyl group.

With the term aryl, either as such or as arylalkyl, arylcarbonyl and the like, we intend a mono-, bi- or poly- either carbocyclic as well as heterocyclic hydrocarbon with from 1 to 4 ring moieties, either fused or linked to each other by single bonds, wherein at least one of the carbocyclic or heterocyclic rings is aromatic.

Examples of aryl groups are phenyl, biphenyl, α- or β-naphthyl, tetrahydronaphthyl, indenyl, dihydroindenyl, pyridyl, pyrazinyl, pyrimidinyl, pyridazinyl, indolyl, isoindolyl, dihydroisoindolyl, imidazolyl, imidazopyridyl, benzimidazolyl, dihydrobenzimidazolyl, 1,2-methylenedioxyphenyl, thiazolyl, isothiazolyl, benzothiazolyl, pyrrolyl, pyrazolyl, furyl, benzotetrahydrofuranyl, benzofuranyl, dihydrobenzofuranyl, oxazolyl, isoxazolyl, thienyl, benzothienyl, tetrazolyl, quinolinyl, isoquinolinyl, dihydroisoquinolinyl, quinoxalinyl, dihdroquinoxalinyl, oxadiazolyl, tetrahydrobenzodiazepin-yl and the like.

With the term 3 to 6 membered carbocycle, hence encompassing but not limited to $C_3$–$C_6$ cycloalkyl groups, we also intend an unsaturated carbocyclic hydrocarbon such as, for instance, cyclopentylene or cyclohexylene.

With the term 5 to 7 membered heterocycle, hence encompassing aromatic heterocycles also referred to as aryl groups, we further intend a saturated or partially unsaturated 5 to 7 membered carbocycle wherein one or more carbon atoms are replaced by heteroatoms such as nitrogen, oxygen and sulphur.

Examples of 5 to 7 membered heterocycles, optionally benzocondensed or further substituted, are 1,3-dioxolane, pyran, pyrrolidine, pyrroline, imidazolidine, pyrazolidine, pyrazoline, piperidine, piperazine, N-alkyl-piperazine, morpholine, tetrahydrofuran, and the like.

With the term bridged heterocycles we intend a system at least comprising two rings, one of which being a nitrogen containing heterocycle, having two or more atoms in common such as, for instance, azabicyclo[3.2.2]nonane.

With the term 9 to 11 membered spiro heterocycle we intend a system at least comprising two rings, one of which being a nitrogen containing heterocycle, having one carbon atom in common such as, for instance, 1,4-dioxa-8-azaspiro[4.5]decane and 1,3,8-triazaspiro[4.5]decane.

According to the above indicated substituent meanings, any of the above R, $R_1$ and $R_2$ groups may be optionally substituted in any of the free positions by one or more groups, for instance 1 to 6 groups, selected from: halogen, nitro, oxo groups (=O), carboxy, cyano, alkyl, perfluorinated alkyl, alkenyl, alkynyl, cycloalkyl, aryl, heterocyclyl, amino groups and derivatives thereof such as, for instance, alkylamino, alkoxycarbonylalkylamino, dialkylamino, arylamino, diarylamino, alkylsulfonylamino or arylureido; carbonylamino groups and derivatives thereof such as, for instance, formylamino, alkylcarbonylamino, alkenylcarbonylamino, arylcarbonylamino, alkoxycarbonylamino; oxygen-substituted oximes such as, for instance, alkoxycarbonylalkoxyimino or alkoxyimino; hydroxy groups and derivatives thereof such as, for instance, alkoxy, aryloxy, alkycarbonyloxy, arylcarbonyloxy, cycloalkenyloxy; carbonyl groups and derivatives thereof such as, for instance, alkylcarbonyl, arylcarbonyl, alkoxycarbonyl, aryloxycarbonyl, cycloalkyloxycarbonyl, aminocarbonyl, alkylaminocarbonyl, dialkylaminocarbonyl; sulfurated derivatives such as, for instance, alkylthio, arylthio, alkylsulphonyl, arylsulphonyl, alkylsulphinyl, arylsulphinyl, arylsulphonyloxy, aminosulfonyl, alkylaminosulphonyl or dialkylaminosulphonyl. In their turn, whenever appropriate, each of the above possible substituents on R, $R_1$ and $R_2$ may be further substituted by one or more of the aforementioned groups.

Examples of compounds of formula (I) wherein R, $R_1$ and $R_2$ groups are substituted by one or more of the aforementioned substituents which, in their turn, are optionally further substituted as set forth above, are given below.

Pharmaceutically acceptable salts of the compounds of formula (I) are the acid addition salts with inorganic or organic, e.g. nitric, hydrochloric, hydrobromic, sulphuric, perchloric, phosphoric, acetic, trifluoroacetic, propionic, glycolic, lactic, oxalic, malonic, malic, maleic, tartaric, citric, benzoic, cinnamic, mandelic, methanesulphonic, isethionic and salicylic acid, as well as the salts with inorganic or organic bases, e.g. alkali or alkaline-earth metals, especially sodium, potassium, calcium or magnesium hydroxides, carbonates or bicarbonates, acyclic or cyclic amines, preferably methylamine, ethylamine, diethylamine, triethylamine or piperidine.

The compounds of formula (I) may have asymmetric carbon atoms and may therefore exist either as racemic admixtures or as individual optical isomers.

Accordingly, the use as an antitumor agent of all the possible isomers and their admixtures and of both the metabolites and the pharmaceutically acceptable bio-precursors (otherwise referred to as pro-drugs) of the compounds of formula (I) are also within the scope of the present invention.

Preferred compounds of the invention are the compounds of formula (I) wherein R is a halogen atom, a straight or branched $C_1$–$C_4$ alkyl group, a phenyl or a cycloalkyl group; $R_2$ is hydrogen and $R_1$ is an optionally substituted group selected from alkyl, aryl or arylalkyl.

Even more preferred, within this class, are the compounds of formula (I) wherein R is bromine or chlorine, a straight or branched $C_1$–$C_4$ alkyl group, a phenyl or a cycloalkyl group; $R_2$ is hydrogen and $R_1$ is an optionally substituted aryl or an arylalkyl or heterocyclyl-alkyl group with from 1 to 4 carbon atoms within the alkyl chain.

Another class of preferred compounds of the invention are compounds of formula (I)

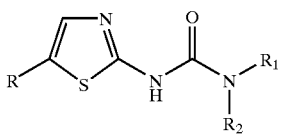

(I)

wherein
R is a halogen atom or is selected from the group consisting of nitro, amino, alkylamino, hydroxyalkylamino, arylamino, $C_3$–$C_6$ cycloalkyl, straight or branched $C_1$–$C_6$ alkyl optionally substituted by hydroxy, alkylthio, alkoxy, amino, alklamino, alkoxycarbonylalkylamino, alkylcarbonyl, alkylsulfonyl, alkoxycarbonyl, carboxy, aryl optionally substituted by one or more hydroxy, halogen, nitro, alkoxy, aryloxy, alkylthio, arylthio, amino, alkylamino, dialkylamino, N-alkyl-piperazinyl, 4-morpholinyl, arylamino, cyano, alkyl, phenyl, aminosulfonyl, aminocarbonyl, alkylcarbonyl, arylcarbonyl, alkoxycarbonyl or carboxy, or R is an aryl group optionally substituted by one or more hydroxy, halogen, nitro, alkoxy, aryloxy, alkylthio, arylthio, amino, alkylamino, dialkylamino, N-alkyl-piperazinyl, 4-morpholinyl, arylamino, cyano, alkyl, phenyl, aminosulphonyl, aminocarbonyl, alkylcarbonyl, arylcarbonyl, alkoxycarbonyl or carboxy;

$R_1$ is a straight or branched $C_1$–$C_6$ alkyl group or an aryl group, each optionally substituted as above reported for R;

$R_2$ is a hydrogen atom; and pharmaceutically acceptable salts thereof; provided that:
a) when R is chlorine or bromine then $R_1$ is not unsubstituted $C_1$–$C_3$ alkyl, phenyl, trifluoromethylphenyl or an optionally substituted phenylcarbonyl;
b) when R is methyl then $R_1$ is not methyl, phenyl or 4-(5-oxazolyl)phenyl;
c) when R is nitrophenyl then $R_1$ is not haloalkyl.

Another class of preferred compounds of formula (I) are those wherein R is a straight or branched $C_1$–$C_6$ alkyl group and, together with the nitrogen atom to which they are bonded, $R_1$ and $R_2$ form a substituted or unsubstituted, optionally either benzocondensed or bridged 5 to 7 membered heterocycle, or 9 to 11 membered spiro-heterocycle.

Still another class of preferred compounds of formula (I) are those wherein R is a straight or branched $C_1$–$C_6$ alkyl group; $R_2$ is a straight or branched $C_1$–$C_4$ alkyl or $C_2$–$C_4$ alkenyl or alkynyl group and $R_1$ is an aryl or arylalkyl group with from 1 to 4 carbon atoms within the straight or branched alkyl chain.

Examples of preferred compounds of the invention, whenever appropriate in the form of pharmaceutically acceptable salts, e.g. hydrobromide or hydrochloride salt, are the following:
1) N-(5-isopropyl-1,3-thiazol-2-yl)-N'-phenyl-urea;
2) N-(5-bromo-1,3-thiazol-2-yl)-N'-phenyl-urea;
3) N-(5-phenyl-1,3-thiazol-2-yl)-N'-phenyl-urea;
4) N-(5-cyclopropyl-1,3-thiazol-2-yl)-N'-phenyl-urea;
5) N-(5-bromo-1,3-thiazol-2-yl)-N'-(4-sulfamoyl-phenyl)-urea;
6) N-(5-isopropyl-1,3-thiazol-2-yl)-N'-(4-sulfamoyl-phenyl)-urea;
7) N-(5-phenyl-1,3-thiazol-2-yl)-N'-(4-sulfamoyl-phenyl)-urea;
8) N-(5-cyclopropyl-1,3-thiazol-2-yl)-N'-(4-sulfamoyl-phenyl)-urea;
9) N-(5-isopropyl-1,3-thiazol-2-yl)-N'-(3-methoxy-phenyl)-urea;
10) N-(5-bromo-1,3-thiazol-2-yl)-N'-(3-methoxy-phenyl)-urea;
11) N-(5-phenyl-1,3-thiazol-2-yl)-N'-(3-methoxy-phenyl)-urea;
12) N-(5-cyclopropyl-1,3-thiazol-2-yl)-N'-(3-methoxy-phenyl)-urea;
13) N-(5-isopropyl-1,3-thiazol-2-yl)-N'-(4-chloro-phenyl)-urea;
14) N-(5-bromo-1,3-thiazol-2-yl)-N'-(4-chloro-phenyl)-urea;
15) N-(5-phenyl-1,3-thiazol-2-yl)-N'-(4-chloro-phenyl)-urea;
16) N-(5-cyclopropyl-1,3-thiazol-2-yl)-N'-(4-chloro-phenyl)-urea;
17) N-(5-isopropyl-1,3-thiazol-2-yl)-N'-(3-chloro-phenyl)-urea;
18) N-(5-bromo-1,3-thiazol-2-yl)-N'-(3-chloro-phenyl)-urea;
19) N-(5-phenyl-1,3-thiazol-2-yl)-N'-(3-chloro-phenyl)-urea;
20) N-(5-cyclopropyl-1,3-thiazol-2-yl)-N'-(3-chloro-phenyl)-urea;
21) N-(5-isopropyl-1,3-thiazol-2-yl)-N'-(2-chloro-phenyl)-urea;
22) N-(5-bromo-1,3-thiazol-2-yl)-N'-(2-chloro-phenyl)-urea;
23) N-(5-phenyl-1,3-thiazol-2-yl)-N'-(2-chloro-phenyl)-urea;
24) N-(5-cyclopropyl-1,3-thiazol-2-yl)-N'-(2-chloro-phenyl)-urea;
25) N-(5-isopropyl-1,3-thiazol-2-yl)-N'-(4-methoxy-phenyl)-urea;
26) N-(5-bromo-1,3-thiazol-2-yl)-N'-(4-methoxy-phenyl)-urea;
27) N-(5-phenyl-1,3-thiazol-2-yl)-N'-(4-methoxy-phenyl)-urea;
28) N-(5-cyclopropyl-1,3-thiazol-2-yl)-N'-(4-methoxy-phenyl)-urea;
29) N-(5-isopropyl-1,3-thiazol-2-yl)-N'-(4-hydroxy-phenyl)-urea;
30) N-(5-bromo-1,3-thiazol-2-yl)-N'-(4-hydroxy-phenyl)-urea;
31) N-(5-phenyl-1,3-thiazol-2-yl)-N'-(4-hydroxy-phenyl)-urea;
32) N-(5-cyclopropyl-1,3-thiazol-2-yl)-N'-(4-hydroxy-phenyl)-urea;
33) N-(5-isopropyl-1,3-thiazol-2-yl)-N'-(3-hydroxy-phenyl)-urea;
34) N-(5-bromo-1,3-thiazol-2-yl)-N'-(3-hydroxy-phenyl)-urea;
35) N-(5-phenyl-1,3-thiazol-2-yl)-N'-(3-hydroxy-phenyl)-urea;
36) N-(5-cyclopropyl-1,3-thiazol-2-yl)-N'-(3-hydroxy-phenyl)-urea;
37) N-(5-isopropyl-1,3-thiazol-2-yl)-N'-(2-methoxy-phenyl)-urea;
38) N-(5-bromo-1,3-thiazol-2-yl)-N'-(2-methoxy-phenyl)-urea;
39) N-(5-phenyl-1,3-thiazol-2-yl)-N'-(2-methoxy-phenyl)-urea;
40) N-(5-cyclopropyl-1,3-thiazol-2-yl)-N'-(2-methoxy-phenyl)-urea;
41) N-(5-isopropyl-1,3-thiazol-2-yl)-N'-(2-hydroxy-phenyl)-urea;

42) N-(5-bromo-1,3-thiazol-2-yl)-N'-(2-hydroxy-phenyl)-urea;
43) N-(5-phenyl-1,3-thiazol-2-yl)-N'-(2-hydroxy-phenyl)-urea;
44) N-(5-cyclopropyl-1,3-thiazol-2-yl)-N'-(2-hydroxy-phenyl)-urea;
45) N-(5-isopropyl-1,3-thiazol-2-yl)-N'-(4-nitro-phenyl)-urea;
46) N-(5-bromo-1,3-thiazol-2-yl)-N'-(4-nitro-phenyl)-urea;
47) N-(5-phenyl-1,3-thiazol-2-yl)-N'-(4-nitro-phenyl)-urea;
48) N-(5-cyclopropyl-1,3-thiazol-2-yl)-N'-(4-nitro-phenyl)-urea;
49) N-(5-isopropyl-1,3-thiazol-2-yl)-N'-(4-amino-phenyl)-urea;
50) N-(5-bromo-1,3-thiazol-2-yl)-N'-(4-amino-phenyl)-urea;
51) N-(5-phenyl-1,3-thiazol-2-yl)-N'-(4-amino-phenyl)-urea;
52) N-(5-cyclopropyl-1,3-thiazol-2-yl)-N'-(4-amino-phenyl)-urea;
53) N-(5-isopropyl-1,3-thiazol-2-yl)-N'-(3-nitro-phenyl)-urea;
54) N-(5-bromo-1,3-thiazol-2-yl)-N'-(3-nitro-phenyl)-urea;
55) N-(5-phenyl-1,3-thiazol-2-yl)-N'-(3-nitro-phenyl)-urea;
56) N-(5-cyclopropyl-1,3-thiazol-2-yl)-N'-(3-nitro-phenyl)-urea;
57) N-(5-isopropyl-1,3-thiazol-2-yl)-N'-(3-amino-phenyl)-urea;
58) N-(5-bromo-1,3-thiazol-2-yl)-N'-(3-amino-phenyl)-urea;
59) N-(5-phenyl-1,3-thiazol-2-yl)-N'-(3-amino-phenyl)-urea;
60) N-(5-cyclopropyl-1,3-thiazol-2-yl)-N'-(3-amino-phenyl)-urea;
61) N-(5-isopropyl-1,3-thiazol-2-yl)-N'-benzyl-urea;
62) N-(5-bromo-1,3-thiazol-2-yl)-N'-benzyl-urea;
63) N-(5-phenyl-1,3-thiazol-2-yl)-N'-benzyl-urea;
64) N-(5-cyclopropyl-1,3-thiazol-2-yl)-N'-benzyl-urea;
65) N-(5-isopropyl-1,3-thiazol-2-yl)-N'-(pyrid-3-yl)-urea;
66) N-(5-bromo-1,3-thiazol-2-yl)-N'-(pyrid-3-yl)-urea;
67) N-(5-phenyl-1,3-thiazol-2-yl)-N'-(pyrid-3-yl)-urea;
68) N-(5-cyclopropyl-1,3-thiazol-2-yl)-N'-(pyrid-3-yl)-urea;
69) N-(5-bromo-1,3-thiazol-2-yl)-N'-(pyrid-4-yl)-urea;
70) N-(5-isopropyl-1,3-thiazol-2-yl)-N'-(pyrid-4-yl)-urea;
71) N-(5-phenyl-1,3-thiazol-2-yl)-N'-(pyrid-4-yl)-urea;
72) N-(5-cyclopropyl-1,3-thiazol-2-yl)-N'-(pyrid-4-yl)-urea;
73) N-(5-isopropyl-1,3-thiazol-2-yl)-N'-(pyrid-2-yl)-urea;
74) N-(5-bromo-1,3-thiazol-2-yl)-N'-(pyrid-2-yl)-urea;
75) N-(5-phenyl-1,3-thiazol-2-yl)-N'-(pyrid-2-yl)-urea;
76) N-(5-cyclopropyl-1,3-thiazol-2-yl)-N'-(pyrid-2-yl)-urea;
77) N-(5-isopropyl-1,3-thiazol-2-yl)-N'-(benzothiophen-2-yl)-urea;
78) N-(5-bromo-1,3-thiazol-2-yl)-N'-(benzothiophen-2-yl)-urea;
79) N-(5-phenyl-1,3-thiazol-2-yl)-N'-(benzothiophen-2-yl)-urea; N-(5-cyclopropyl-1,3-thiazol-2-yl)-N'-(benzothiophen-2-yl)-urea;
80) N-(5-isopropyl-1,3-thiazol-2-yl)-4-morpholine carboxamide;
81) N-(5-isopropyl-1,3-thiazol-2-yl)-N'-(4-methylphenyl) urea;
82) N-(5-isopropyl-1,3-thiazol-2-yl)-N'-(3-fluorophenyl) urea;
83) N-(5-isopropyl-1,3-thiazol-2-yl)-N'-(4-cyanophenyl) urea;
84) N-(5-isopropyl-1,3-thiazol-2-yl)-N'-(3-cyanophenyl) urea;
85) N-(5-isopropyl-1,3-thiazol-2-yl)-N'-(2,6-dimethylphenyl)urea;
86) N-(5-isopropyl-1,3-thiazol-2-yl)-N'-(4-fluorobenzyl) urea;
87) N-(5-isopropyl-1,3-thiazol-2-yl)-N'-(3-acetylphenyl) urea;
88) N-(5-isopropyl-1,3-thiazol-2-yl)-N'-(4-acetylphenyl) urea;
89) 3-({[(5-isopropyl-1,3-thiazol-2-yl)amino]carbonyl}amino)benzoic acid;
90) N-(5-isopropyl-1,3-thiazol-2-yl)-N'-(4-isopropylphenyl)urea;
91) 3-({[(5-isopropyl-1,3-thiazol-2-yl)amino]carbonyl}amino)benzamide;
92) N-(5-isopropyl-1,3-thiazol-2-yl)-N'(4-methoxybenzyl) urea;
93) N-(5-isopropyl-1,3-thiazol-2-yl)-N'-(4-butylphenyl) urea;
94) N-(5-isopropyl-1,3-thiazol-2-yl)-N'-(4-trifluoromethylphenyl)urea;
95) N-(5-isopropyl-1,3-thiazol-2-yl)-N'-3-bromophenyl) urea;
96) N-(5-isopropyl-1,3-thiazol-2-yl)-N'-(4-cyclohexylphenyl)urea;
97) N-(5-isopropyl-1,3-thiazol-2-yl)-N'-(4-phenoxyphenyl) urea;
98) N-(5-isopropyl-1,3-thiazol-2-yl)-N'-(4-benzloxyphenyl) urea;
99) N-(5-isopropyl-1,3-thiazol-2-yl)-N'-(3,5-dimethylphenyl)urea;
100) N-(5-isopropyl-1,3-thiazol-2-yl)-N'-(2,3-dimethylphenyl)urea;
101) N-(5-isopropyl-1,3-thiazol-2-yl)-N'-(3-methoxy[1,1-biphenyl]-4-yl)urea;
102) N-(5-isopropyl-1,3-thiazol-2-yl)-3,4-dihydro-2(1H)-isoquinoline carboxamide;
103) N-benzyl-N'-(5-isopropyl-1,3-thiazol-2-yl)-N-methylurea;
104) N-(5-isopropyl-1,3-thiazol-2-yl)-6,7-dimethoxy-3,4-dihydro-2(1H)-isoquinoline carboxamide;
105) N-(5-isopropyl-1,3-thiazol-2-yl)-N'-[(3-chloro-4-methyl)-phenyl]urea;
106) N-(5-isopropyl-1,3-thiazol-2-yl)-N'-[(3-chloro-6-methyl)phenyl]urea;
107) N-(5-isopropyl-1,3-thiazol-2-yl)-N'-(2,5-dimethoxyphenyl)urea;
108) N-(5-isopropyl-1,3-thiazol-2-yl)-N'-(3,4-dimethoxyphenyl)urea;
109) N-(5-isopropyl-1,3-thiazol-2-yl)-N'-[(2-methoxy-5-chloro)phenyl]urea;
110) N-(5-isopropyl-1,3-thiazol-2-yl)-N'-((2-chloro-4-methoxyphenyl)urea;
111) N-(5-isopropyl-1,3-thiazol-2-yl)-N'-(3,5-dichlorophenyl)urea;
112) N-[(1,1'-biphenyl)-2-yl]-N'-(5-isopropyl-1,3-thiazol-2-yl)urea;
113) N-ethyl-N'-(5-isopropyl-1,3-thiazol-2-yl)-N-phenylurea;
114) N-[4-({[(5-isopropyl-1,3-thiazol-2-yl)amino]carbonyl}amino)-2-methoxyphenyl]acetamide;
115) 2-({[(5-isopropyl-1,3-thiazol-2-yl)amino]carbonyl}amino)-N-phenylbenzamide;
116) N-(5-isopropyl-1,3-thiazol-2-yl)-N'-(2-morpholinophenyl)urea;
117) N-[4-({[(5-isopropyl-1,3-thiazol-2-yl)amino]carbonyl}amino)phenyl]-N-methyl acetamide;

118) N-(2-{[cyclohexyl(methyl)amino]methyl}phenyl)-N'-(5-isopropyl-1,3-thiazol-2-yl)urea;
119) N-[3-({[(5-isopropyl-1,3-thiazol-2-yl)amino]carbonyl}amino)-4-methoxyphenyl]acetamide;
120) N-(5-isopropyl-1,3-thiazol-2-yl)-4-(4-methoxyphenyl)-1-piperazine carboxamide;
121) N-(2-furylmethyl)-N'-(5-isopropyl-1,3-thiazol-2-yl)urea;
122) N-(4-fluorophenyl)-N'-(5-isopropyl-1,3-thiazol-2-yl)urea;
123) N-(2-methoxybenzyl)-N'-(5-isopropyl-1,3-thiazol-2-yl)urea;
124) N-(5-isopropyl-1,3-thiazol-2-yl)-N'-[2-(1-methyl-1H-pyrrol-2-yl)ethyl]urea;
125) N-(3,4-dimethoxybenzyl)-N'-(5-isopropyl-1,3-thiazol-2-yl)urea;
126) N-(5-isopropyl-1,3-thiazol-2-yl)-4-oxo-1-phenyl-1,3,8-triazaspiro[4.5]decane-8-carboxamide;
127) n-(5-isopropyl-1,3-thiazol-2-yl)-1,4-dioxa-8-azaspiro[4.5]decane-8-carboxamide;
128) N-(5-isopropyl-1,3-thiazol-2-yl)-N'-[2-(1-piperidinyl)ethyl]urea;
129) N-(5-isopropyl-1,3-thiazol-2-yl)-N'-[2-(1-morpholinyl)ethyl]urea;
130) 4-(4-fluorophenyl)-N-(5-isopropyl-1,3-thiazol-2-yl)-1-piperazine carboxamide;
131) N-[4-(4-chlorophenyl)-3-ethyl-5-isoxazolyl]-N'-(5-isopropyl-1,3-thiazol-2-yl)urea;
132) 4-[(4-fluorophenyl)(hydroxy)methyl]-N-(5-isopropyl-1,3-thiazol-2-yl)-1-piperidine carboxamide;
133) N-(3-ethynylphenyl)-N'-(5-isopropyl-1,3-thiazol-2-yl)urea;
134) N-(2-methoxy-3-fluorophenyl)-N'-(5-isopropyl-1,3-thiazol-2-yl)urea;
135) N-(5-isopropyl-1,3-thiazol-2-yl)-N'-(4-oxo-1-piperidinyl)urea;
136) N-(3-acetylaminophenyl)-N'-(5-isopropyl-1,3-thiazol-2-yl)urea;
137) N-[3-(2-furyl)-1H-pyrazol-5-yl]-N'-(5-isopropyl-1,3-thiazol-2-yl)urea;
138) N-{4-[ethyl(isopropyl)amino]phenyl}-N'-(5-isopropyl-1,3-thiazol-2-yl)urea;
139) N-(1,3-benzodioxol-5-yl)-N'-(5-isopropyl-1,3-thiazol-2-yl)urea;
140) 5-({[(5-isopropyl-1,3-thiazol-2-yl)amino]carbonyl}amino)-1-phenyl-1H-pyrazole-4-carboxamide;
141) N-(5-isopropyl-1,3-thiazol-2-yl)-N'-(4-pyridinylmethyl)urea;
142) N-(5-isopropyl-1,3-thiazol-2-yl)-N'-(2-pyrazinyl)urea;
143) n-(5-isopropyl-1,3-thiazol-2-yl)-N'-(5-phenyl-1,3,4-oxadiazol-2-yl)urea;
144) N-(5-isopropyl-1,3-thiazol-2-yl)-4-(2-oxo-2,3-dihydro-1H-benzimidazol-1-yl)-1-piperidine carboxamide;
145) N-(1,3-benzothiazol-6-yl)-N'-(5-isopropyl-1,3-thiazol-2-yl)area;
146) N-(1,3-dimethyl-1H-pyrazol-5-yl)-N'-(5-isopropyl-1,3-thiazol-2-yl)urea;
147) N-(3-phenyl-1-methyl-1H-pyrazol-5-yl)-N'-(5-isopropyl-1,3-thiazol-2-yl)urea;
148) N-(5-isopropyl-1,3-thiazol-2-yl)-3-hydroxy-1-piperidine carboxamide;
149) N-(5-isopropyl-1,3-thiazol-2-yl)-N'-(2-methyl-1,3-dioxo-2,3-dihydro-1H-isoindol-5-yl)urea;
150) N-(5-isopropyl-1,3-thiazol-2-yl)-4-benzyl-1-piperazine carboxamide;
151) N-(5-isopropyl-1,3-thiazol-2-yl)-4-methyl-1-piperazine carboxamide;
152) 4-hydroxy-N-(5-isopropyl-1,3-thiazol-2-yl)-1-piperazine carboxmide;
153) N-(5-isopropyl-1,3-thiazol-2-yl)-3-azabicyclo[3.2.2]nonane-3-carboxamide;
154) N-(5-isopropyl-1,3-thiazol-2-yl)-4-(4-acetylphenyl)-1-piperazine carboxamide;
155) 4-[bis(4-fluorphenyl)-N-(5-isopropyl-1,3-thiazol-2-yl)-1-piperazine carboxmide;
156) N-(5-isopropyl-1,3-thiazol-2-yl)-4-oxo-2,3,4,5-tetrahydro-1H-1,5-benzodiazepine-1-carboxamide;
157) N-(5-isopropyl-1,3-thiazol-2-yl)-N'-(5,6,7,8-tetrahydro-1-naphtalenyl)urea;
158) N-(4-phenyl-2-thiazolyl)-N'-(5-isopropyl-1,3-thiazol-2-yl)urea;
159) 4-(4-fluorobenzoyl)-N-(5-isopropyl-1,3-thiazol-2-yl)-1-piperidine carboxamide;
160) N-(5-isopropyl-1,3-thiazol-2-yl)-N'-1,3-dihydro-2-benzofuran-5-yl)urea;
161) N-(5-isopropyl-1,3-thiazol-2-yl)-4'-(2-pyrimidinyl)-1-piperazine carboxamide;
162) N-(5-isopropyl-1,3-thiazol-2-yl)-3-oxo-3,4-dihydro-1(2H)-quinoxaline;
163) N-(5-isopropyl-1,3-thiazol-2-yl)-N'-(1H-indazol-6-yl)urea;
164) N-(5-isopropyl-1,3-thiazol-2-yl)-N'-(2-chlorobenzyl)urea;
165) N-(5-isopropyl-1,3-thiazol-2-yl)-N'-(2,4-dichlorobenzyl)urea;
166) N-(5-isopropyl-1,3-thiazol-2-yl)-N'-(3-fluorobenzyl)urea;
167) N-(5-isopropyl-1,3-thiazol-2-yl)-N'-(3,4-dichlorobenzyl)urea;
168) N-(5-isopropyl-1,3-thiazol-2-yl)-N'-(2,4-difluorobenzyl)urea;
169) N-(5-isopropyl-1,3-thiazol-2-yl)-N'-(2,5-difluorobenzyl)urea;
170) N-(5-isopropyl-1,3-thiazol-2-yl)-N'-2,6-difluorobenzyl)urea;
171) N-(5-isopropyl-1,3-thiazol-2-yl)-N'-[(4-hydroxy-3-methoxy)benzyl]urea;
172) N-(5-isopropyl-1,3-thiazol-2-yl)-N'-(5-methyl-2-furyl)urea;
173) N-(5-isopropyl-1,3-thiazol-2-yl)-N'-(4-methylsulfonylbenzyl)urea;
174) N-[(1R,2R)-2-hydroxy-2,3-dihydro-1H-inden-1-yl]-N'-(5-isopropyl-1,3-thiazol-2-yl)urea;
175) N-(5-isopropyl-1,3-thiazol-2-yl)-N'-(4-chlorobenzyl)urea;
176) N-(5-isopropyl-1,3-thiazol-2-yl)-N'-(2-pyridinylmethyl)urea;
177) N-(5-isopropyl-1,3-thiazol-2-yl)-N'-(3,5-dimethoxybenzyl)urea;
178) N-(5-isopropyl-1,3-thiazol-2-yl)-N'-(3-pyridinylmethyl)urea;
179) N-(5-isopropyl-1,3-thiazol-2-yl)-N'-(4-trifluorobenzyl)urea;
180) N-(5-isopropyl-1,3-thiazol-2-yl)-N'-(3,4,5-trimethoxybenzyl)urea;
181) N-(5-isopropyl-1,3-thiazol-2-yl)-N'-(2,4-dimethoxybenzyl)urea;
182) N-(5-isopropyl-1,3-thiazol-2-yl)-N'-(4-dimethylaminobenzyl)urea;
183) N-(5-isopropyl-1,3-thiazol-2-yl)-N'-(2,5-dimethoxybenzyl)urea;
184) N-(5-isopropyl-1,3-thiazol-2-yl)-N'-[(2-chloro-6-phenoxy)benzyl]urea;
185) N-(5-isopropyl-1,3-thiazol-2-yl)-N'-[(1R,2S)-2-hydroxy-2,3-dihydro-1H-inden-1-yl]urea;

186) N-(5-isopropyl-1,3-thiazol-2-yl)-N'-[(3-hydroxy-4-methyl)phenyl]urea;
187) N-(5-isopropyl-1,3-thiazol-2-yl)-N'-[4-(1H-benzimidazol-2-yl)phenyl]urea;
188) N-(5-isopropyl-1,3-thiazol-2-yl)-N'-(3-phenyl-1H-pyrazol-5-yl)urea;
189) N-(5-isopropyl-1,3-thiazol-2-yl)-N'-(2-methyl-6-quinolinyl)urea;
190) N-(5-isopropyl-1,3-thiazol-2-yl)-N'-[4-(cyanomethyl)phenyl]urea;
191) N-(5-isopropyl-1,3-thiazol-2-yl)-N'-(2-quinolinyl)urea;
192) N-(5-isopropyl-1,3-thiazol-2-yl)-N'-(1-oxo-2,3-dihydro-1H-inden-5-yl)urea;
193) N-(5-isopropyl-1,3-thiazol-2-yl)-N'-(3-oxo-1,3-dihydro-2-benzofuran-5-yl)urea;
194) N-(5-isopropyl-1,3-thiazol-2-yl)-N'-(5-oxo-5,6,7,8-tetrahydro-2-naphtalenyl)urea;
195) methyl-3-({[(5-isopropyl-1,3-thiazol-2-yl)amino]carbonyl}amino)-4-methylbenzoate;
196) methyl-4-({[(5-isopropyl-1,3-thiazol-2-yl)amino]carbonyl}amino)-3-methylbenzoate;
197) N-(5-isopropyl-1,3-thiazol-2-yl)-N'-(4-imidazo[1,2-a]pyridin-2-yl-phenyl)urea;
198) ethyl-4-({[(5-isopropyl-1,3-thiazol-2-yl)amino]carbonyl}amino)benzoate;
199) (2R)-1-benzyl-2-({[(5-isopropyl-1,3-thiazol-2-yl)amino]carbonyl}amino)propanamide;
200) 2-hydroxy-5-({[(5-isopropyl-1,3-thiazol-2-yl)amino]carbonyl}benzoic acid;
201) 2-chloro-5-({[(5-isopropyl-1,3-thiazol-2-yl)amino]carbonyl}amino)benzoic acid;
202) 3-({[(5-isopropyl-1,3-thiazol-2-yl)amino]carbonyl}amino)benzoic acid;
203) N-(5-isopropyl-1,3-thiazol-2-yl)-N'-(5-methyl-3-isoxazolyl)urea;
204) N-(5-isopropyl-1,3-thiazol-2-yl)-N'-(2,6-dimethoxyphenyl)urea;
205) N-(5-isopropyl-1,3-thiazol-2-yl)-N'-(2,3-dimethoxybenzyl)urea;
206) N-(5-isopropyl-1,3-thiazol-2-yl)-N'-(3,4-difluorobenzyl)urea;
207) N-(5-isopropyl-1,3-thiazol-2-yl)-N'-(2,4-dimethylphenyl)urea;
208) N-(5-isopropyl-1,3-thiazol-2-yl)-N'-(1H-benzimidazol-5-yl)urea;
209) N-(5-isopropyl-1,3-thiazol-2-yl)-N'-[(R)-phenylglicinamido]urea;
210) N-(5-isopropyl-1,3-thiazol-2-yl)-N'-(2-phenoxyacetamido)urea;
211) N-(5-isopropyl-1,3-thiazol-2-yl)-N'-{(S)-phenylglicinamido}urea;
212) N-(5-isopropyl-1,3-thiazol-2-yl)-N'-{2-[(1-methyl-1H-imidazol-2-yl)methoxy]phenyl}urea;
213) N-(3-iodophenyl)-N'-(5-isopropyl-1,3-thiazol-2-yl)urea;
214) N-(5-isopropyl-1,3-thiazol-2-yl)-N'-[3-(3-methoxy-1-propynyl)phenyl]urea;
215) N-{3-[3-(dimethylamino)-1-propynyl]phenyl}-N'-(5-isopropyl-1,3-thiazol-2-yl)urea;
216) N-[4-({[(5-isopropyl-1,3-thiazol-2-yl)amino]carbonyl}amino)phenyl]methanesulfonamide;
217) 2-[3-({[(5-isopropyl-1,3-thiazol-2-yl)amino]carbonyl}amino)anilino]acetamide;
218) N-[3-(3-hydroxy-1-butynyl)phenyl]-N'-(5-isopropyl-1,3-thiazol-2-yl)urea;
219) N-(imidazo[1,2-a]pyridin-2-yl-methyl)-N'-(5-isopropyl-1,3-thiazol-2-yl)urea;
220) 2-{[{[(5-isopropyl-1,3-thiazol-2-yl)amino]carbonyl}(2-propynyl)amino]methyl}benzenesulfonamide;
221) N-(1H-indol-6-yl)-N'-(5-isopropyl-1,3-thiazol-2-yl)urea;
222) N-[(1S)-2-hydroxy-1-phenylethyl]-N'-(5-isopropyl-1,3-thiazol-2-yl)urea;
223) N-(1H-indol-5-yl)-N'-(5-isopropyl-1,3-thiazol-2-yl)urea;
224) N-[(1R-2-hydroxy-1-phenylethyl]-N'-(5-isopropyl-1,3-thiazol-2-yl)urea;
225) N-(5-isopropyl-1,3-thiazol-2-yl)-N'-butylurea;
226) N-(5-isopropyl-1,3-thiazol-2-yl)-N'-benzoylurea;
227) N-(5-methyl-1,3-thiazol-2-yl)-N'-(2,6-dimethylphenyl)urea;
228) N-(5-methyl-1,3-thiazol-2-yl)-N'-benzylurea;
229) N-(5-methyl-1,3-thiazol-2-yl)-N'-butylurea;
230) N-(5-methyl-1,3-thiazol-2-yl)-4-morpholinecarboxamide;
231) N-(5-methyl-1,3-thiazol-2-yl)-N'-phenylurea;
232) N-(5-methyl-1,3-thiazol-2-yl)N'-(4-methoxybenzylurea;
233) N-(5-methyl-1,3-thiazol-2-yl)-N'-(4-fluorophenyl)urea;
234) N-[(1-ethyl-2-pyrrolidinyl)methyl]-N'-(5-methyl-1,3-thiazol-2-yl)urea;
235) N-(5-methyl-1,3-thiazol-2-yl)-N'-(5-hydroxy-1H-pyrazol-3-yl)urea;
236) N-(5-methyl-1,3-thiazol-2-yl)-N'-(3-pyridinyl)urea;
237) N-(4-fluorophenyl)-N'-(5-isopropyl-1,3-thiazol-2-yl)urea.

The compounds of formula (I) object of the present invention and the salts thereof can be obtained, for instance, by a process comprising:

a) when $R_2$ is a hydrogen atom
reacting a compound of formula (II)

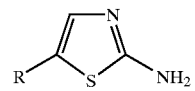

(II)

wherein R is as defined above, with a compound of formula (III)

$R_1$—NCO  (III)

wherein $R_1$ is as defined above; or b) when $R_2$ is a hydrogen atom or has the meanings above reported
reacting a compound of formula (IV)

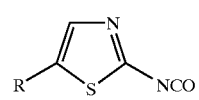

(IV)

wherein R is as defined above, with a compound of formula (V)

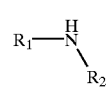

(V)

wherein $R_1$ and $R_2$ are as defined above; and, if desired, converting a 2-ureido-1,3-thiazole derivative of formula (I) into another such derivative of formula (I), and/or into a salt thereof.

The compounds of formula (I) can alternatively be obtained by a process comprising:
reacting a compound of formula (II) wherein R is as described above with 4-nitrophenyl-chloroformate, or a polymer supported form of it, thus obtaining a compound of formula (VI), or a polymer supported form of it,

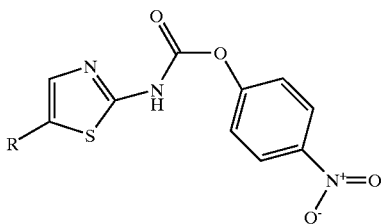

wherein R is as described above; and reacting a compound of formula (VI) with a compound of formula (V)

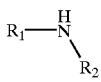

wherein $R_1$ and $R_2$ are as described above; and, if desired, converting a 2-ureido-1,3-thiazole derivative of formula (I), or a polymer supported form of it, into another such derivative of formula (I), and/or into a salt thereof.

More particularly, when referring to the process performed by using polymer supported species, the synthetic pathway can be summarized as follows:

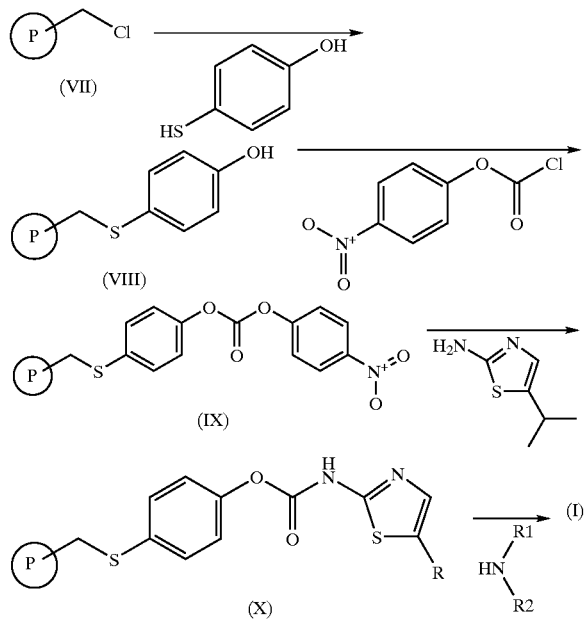

In addition, when referring to the process performed by using polymer supported species, conventional reaction conditions are well known to the skilled man.

It is further clear to the man skilled in the art that if the compound of formula (I), prepared according to the above processes, is obtained as an admixture of isomers, their separation into the single isomers of formula (I) according to conventional techniques is still within the scope of the present invention.

Likewise, the conversion into the free 2-ureido-1,3-thiazole derivative (I) of a corresponding salt thereof, according to well-known procedures in the art, is still within the scope of the invention.

The above process-variants are analogy processes which can be carried out according to well known methods.

The reaction between a compound of formula (II) and a compound of formula (III), or the reaction between a compound of formula (IV) and a compound of formula (V), can be carried out in a suitable solvent such as, for instance, dichloromethane, chloroform, tetrahydrofuran, diethyl ether, 1,4-dioxane, acetonitrile, toluene or acetone, at a temperature ranging from room temperature to reflux for a time varying between about 1 to 96 hours.

The reaction of a compound of formula (II) to give a compound of formula (VI) is carried out with 4-nitrophenylchloroformate, or a polymer supported form of it, in the presence of a tertiary base such as, for instance, triethylamine, N-methylmorpholine, N,N-diisopropylethylamine or pyridine, in a suitable solvent such as toluene, dichloromethane, chloroform, diethylether, tetrahydrofuran, acetonitrile, dioxane or N,N-dimethylformamide, at a temperature ranging from approximately −10° C. to room temperature.

The reaction between a compound of formula (VI) and a compound of formula (V) to give a compound of formula (I) can be carried out in a suitable solvent such as toluene, dichloromethane, chloroform, diethylether, tetrahydrofuran, acetonitrile, 1,4-dioxane or N,N-dimethylformamide, at a temperature ranging from about room temperature to reflux. In the above-mentioned scheme, as far as the solid phase approach is concerned, compound (VIII) can be prepared by reacting compound (VII) with 4-mercaptophenol in the presence of a base such as potassium tert-butoxide, potassium carbonate or potassium sodium hydroxide and in a suitable solvent such as N,N-dimethylformamide at a temperature ranging from 40 to 60° C. The reaction between compound (VIII) and p-nitrophenylchloroformate to give compound (IX) can be carried out in presence of a base such as N-methylmorpholine, triethylamine or N,N-diisopropyethylamine in a suitable solvent such as dichloromethane, chloroform, 1,4-dioxane or N,N-dimethylformamide at room temperature.

The reaction between compound (IX) and the compound of formula (II), wherein R is as described above, thus obtaining the compound of formula (X), can be carried out in a suitable solvent such as dichloromethane, chloroform, toluene or N,N-dimethylformamide at room temperature for a time varying between about 2 to 22 hours.

The reaction between the compound of formula (X), wherein R is as described above, and the compound of formula (V) wherein $R_1$ and $R_2$ are as described above, thus obtaining the compound of formula (I), can be carried out in the presence of a base such as triethylamine, N,N-diisopropylethylamine or N-methylmorpholine in a suitable solvent such as toluene, acetonitrile or N,N-dimethylformamide at a temperature ranging from room temperature to 100° C.

Also the optional conversion of a compound of formula (I) into another compound of formula (I) can be carried out according to known methods.

As an example, the nitro group of a compound of formula (I) may be converted into an amino group by treatment, for example, with stannous chloride in concentrated hydrochloric acid and by using, if necessary, an organic solvent such as acetic acid, 1,4-dioxane and tetrahydrofuran, at a temperature varying between room temperature and about 100° C.

Likewise, an alkylthio or an arylthio group may be converted into the corresponding alkylsulfonyl and arylsulfonyl group by reaction, for example, with m-chloroperbenzoic acid in a suitable solvent such as dichloromethane or chloroform, at a temperature varying from about −5° C. and room temperature.

The optional salification of a compound of formula (I) or the conversion of a salt into the free compound as well as the separation of a mixture of isomers into the single isomers may be carried out by conventional methods.

The compounds of formula (II) and (IV) according to the above processes are known compounds or can be obtained according to known methods.

For example, a compound of formula (II) wherein R is as defined above can be obtained by reacting a compound of formula (XI)

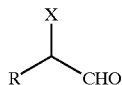

(XI)

wherein X is a bromine or chlorine atom, with thiourea in a suitable solvent such as methanol, ethanol, tetrahydrofuran, 1,4-dioxane or toluene, at a temperature varying between room temperature and reflux, for a suitable time ranging from about 1 hour to about 24 hours.

A compound of formula (IV) can be obtained, for instance, by reacting a compound of formula (II) wherein R is as defined above with bis(trichloromethyl) carbonate or trichloromethyl chloroformate in the presence, if necessary, of a tertiary base such as triethylamine, N,N-diisopropylethylamine or pyridine, in a suitable solvent such as dichloromethane, chloroform or toluene, at a temperature ranging from about −20° C. to reflux.

The compounds of formula (III), (V) and (XI) are well-known commercially available compounds or, alternatively, may be conventionally prepared according to known methods in organic chemistry.

When preparing the compounds of formula (I) according to the process object of the present invention, optional functional groups within both the starting materials or the intermediates thereof, which could give rise to unwanted side reactions, need to be properly protected according to conventional techniques.

Likewise, the conversion of these latter into the free deprotected compounds may be carried out according to known procedures.

Pharmacology

The compounds of formula (I) are active as cdk/cyclin inhibitors as they gave positive results when tested according to the following procedure.

The compounds of formula (I) are therefore useful to restrict the unregulated proliferation of tumor cells, hence in therapy in the treatment of various tumors such as, for instance, carcinomas, e.g. mammary carcinoma, lung carcinoma, bladder carcinoma, colon carcinoma, ovary and endometrial tumors, sarcomas, e.g. soft tissue and bone sarcomas, and the hematological malignancies such as, e.g., leukemias.

In addition, the compounds of formula (I) are also useful in the treatment of other cell proliferative disorders such as psoriasis, vascular smooth cell proliferation associated with atherosclerosis and post-surgical stenosis and restenosis and in the treatment of Alzheimer's disease.

The inhibiting activity of putative cdk/cyclin inhibitors and the potency of selected compounds was determined through a method of assay based on the use of the MultiScreen-PH 96 well plate (Millipore), in which a phosphocellulose filter paper was placed at each well bottom allowing binding of positive charged substrate after a washing/filtration step.

When a radioactivity labelled phosphate moiety was transferred by the ser/threo kinase to the filter-bound histone, light emitted was measured in a scintillation counter.

The inhibition assay of cdk2/Cyclin A activity was performed according to the following protocol:

Kinase reaction: 1.5 μM histone H1 substrate, 25 μM ATP (0.5 μCi $P^{33}\gamma$-ATP), 30 ng Cyclin A/cdk2 complex, 10 μM inhibitor in a final volume of 100 μl buffer (TRIS HCl 10 mM pH 7.5, $MgCl_2$ 10 mM, 7.5 mM DTT) were added to each well of a 96 U bottom well plate. After 10 min at 37° C. incubation, reaction was stopped by 20 μl EDTA 120 mM.

Capture: 100 μl were transferred from each well to MultiScreen plate, to allow substrate binding to phosphocellulose filter. Plates were then washed 3 times with 150 μl/well PBS $Ca^{++}/Mg^{++}$ free and filtered by MultiScreen filtration system.

Detection: filters were allowed to dry at 37° C., then 100 μl/well scintillant were added and $^{33}P$ labelled histone H1 was detected by radioactivity counting in the Top-Count instrument.

Results: data were analysed and expressed as % inhibition referred to total activity of enzyme (=100%).

All compounds showing inhibition≧50% were further analysed in order to study and define potency (IC50) as well as the kinetic-profile of inhibitor through Ki calculation.

IC50 determination: the protocol used was the same described above, where inhibitors were tested at concentrations ranging from 0.0045 to 10 μM. Experimental data were analyzed by the computer program Graph-Pad Prizm.

Ki calculation: either the concentration of ATP and histone H1 substrate were varied: 4, 8, 12, 24, 48 μM for ATP (containing proportionally diluted $P^{33}\gamma$-ATP) and 0.4, 0.8, 1.2, 2.4, 4.8 μM for histone were used in absence and presence of two different, properly chosen inhibitor concentrations.

Experimental data were analysed by the computer program SigmaPlot for Ki determination, using a random bireactant system equation:

$$v = \frac{V\max \frac{(A)(B)}{aK_A K_B}}{1 + \frac{(A)}{K_A} + \frac{(B)}{K_B} + \frac{(A)(B)}{aK_A K_B}}$$

where A=ATP and B=histone H1.

Following the method above described, a representative compound of formula (I) of the invention, which is N-(5-isopropyl-1,3-thiazol-2-yl)-N'-(3,5-dimethylphenyl)urea, showed an inhibiting activity towards the cdk2/cyclin A complex corresponding to 0.56 μM (IC50).

In addition, the inhibiting activity of putative cdk/cyclin inhibitors and the potency of selected compounds was determined through a method of assay based on the use of a SPA (Scintillation Proximity Assay) 96 well plate assay. The assay is based on the ability of streptavidin coated SPA beads to capture a biotinylated peptide derived from a phosphorylation site of histone.

When a radioactivity labelled phosphate moiety was transferred by the ser/threo kinase to the biotinylated histone peptide, light emitted was measured in a scintillation counter.

The inhibition assay of cdk5/p25 activity was performed according to the following protocol:

Kinase reaction: 1.0 μM biotinylated histone peptide substrate, 0.25 uCi P33g-ATP, 4 nm cdk2/p25 complex, 0–100 μM inhibitor in a final volume of 100 μl buffer (Hepes 20 mM pH 7.5, MgC12 15 mM, 1 mM DTT) were added to each well of a 96 U bottom well plate.

After 20 min at 37° C. incubation, the reaction was stopped by the addition of 500 ug SPA beads in phosphate-buffered saline containing 0.1% Triton X-100, 50 uM ATP and 5 mM EDTA. The beads were allowed to settle, and the radioactivity incorporated in the 33P-labelled peptide was detected in a Top Count scintillation counter.

Results: Data were analyzed and expressed as % Inhibition using the formula:

$$100 \times (1-(\text{Unknown}-\text{Bkgd})/(\text{Enz. Control}-\text{Bkgd}))$$

IC50 values were calculated using a variation of the four parameter logistics equation:

$$Y=100/[1+10^{((\text{Log EC50}-X)*\text{Slope})}]$$

Where $X=\log(\text{uM})$ and $Y=\%$ Inhibition.

The compounds of formula (I) are therefore useful to restrict the unregulated proliferation of tumor cells, hence in therapy in the treatment of various tumors such as, for instance, carcinomas, e.g. mammary carcinoma, lung carcinoma, bladder carcinoma, colon carcinoma, ovary and endometrial tumors, sarcomas, e.g. soft tissue and bone sarcomas, and the hematological malignancies such as, e.g., leukemias.

In addition, the compounds of formula (I) are also useful in the treatment of other cell proliferative disorders such as psoriasis, vascular smooth cell proliferation associated with atherosclerosis and post-surgical stenosis and restenosis and in the treatment of Alzheimer's disease.

The compounds of the present invention can be administered either as single agents or, alternatively, in combination with known anticancer treatments such as radiation therapy or chemotherapy regimen in combination with cytostatic or cytotoxic agents.

As an example, the above compounds can be administered in combination with one or more chemotherapeutic agents such as, for instance, taxane, taxane derivatives, CPT-11, camptothecin derivatives, anthracycline glycosides, e.g. doxorubiein or epirubicin, etoposide, navelbine, vinblastine, carboplatin, cisplatin and the like, optionally within liposomal formulations thereof.

The compounds of formula (I) of the present invention, suitable for administration to a mammal, e.g. to humans, can be administered by the usual routes and the dosage level depends upon the age, weight, conditions of the patient and the administration route.

For example, a suitable dosage adopted for oral administration of a compound of formula (I) may range from about 10 to about 500 mg pro dose, from 1 to 5 times daily. The compounds of the invention can be administered in a variety of dosage forms, e.g. orally, in the form of tablets, capsules, sugar or film coated tablets, liquid solutions or suspensions; rectally in the form of suppositories; parenterally, e.g. intramuscularly, or by intravenous and/or intrathecal and/or intraspinal injection or infusion.

The present invention also includes pharmaceutical compositions comprising a compound of formula (I), or a pharmaceutically acceptable salt thereof, in association with a pharmaceutically acceptable excipient (which can be a carrier or a diluent).

The pharmaceutical compositions containing the compounds of the invention are usually prepared following conventional methods and are administered in a pharmaceutically suitable form.

For example, the solid oral forms may contain, together with the active compound, diluents, e.g. lactose, dextrose, saccharose, sucrose, cellulose, corn starch or potato starch; lubricants, e.g. silica, talc, stearic acid, magnesium or calcium stearate, and/or polyethylene glycols; binding agents, e.g. starches, arabic gum, gelatine, methylcellulose, carboxymethylcellulose or polyvinyl pyrrolidone; disaggregating agents, e.g. a starch, alginic acid, alginates or sodium starch glycolate; effervescing mixtures; dyestuffs; sweeteners; wetting agents such as lecithin, polysorbates, laurylsulphates; and, in general, non-toxic and pharmacologically inactive substances used in pharmaceutical formulations. Said pharmaceutical preparations may be manufactured in known manner, for example, by means of mixing, granulating, tabletting, sugar-coating, or film-coating processes.

The liquid dispersions for oral administration may be e.g. syrups, emulsions and suspensions.

The syrups may contain as carrier, for example, saccharose or saccharose with glycerine and/or mannitol and/or sorbitol.

The suspensions and the emulsions may contain as carrier, for examples a natural gum, agar, sodium alginate, pectin, methylcellulose, carboxymethylcellulose, or polyvinyl alcohol.

The suspension or solutions for intramuscular injections may contain, together with the active compound, a pharmaceutically acceptable carrier, e.g. sterile water, olive oil, ethyl oleate, glycols, e.g. propylene glycol, and, if desired, a suitable amount of lidocaine hydrochloride. The solutions for intravenous injections or infusions may contain as carrier, for example, sterile water or preferably they may be in the form of sterile, aqueous, isotonic saline solutions or they may contain as a carrier propylene glycol.

The suppositories may contain together with the active compound a pharmaceutically acceptable carrier, e.g. cocoa butter, polyethylene glycol, a polyoxyethylene sorbitan fatty acid ester surfactant or lecithin.

The following examples illustrate but do not limit the present invention.

EXAMPLE 1

Preparation of Methyl Cyclopropylacetate

Cyclopropylacetic acid (1.08 g; 10.57 mmol) was dissolved in 50 ml of methanol. The solution was cooled to 0° C. and 5 ml of sulfuric acid 96% were dropped under stirring. The solution was maintained at room temperature overnight and then poured onto ice-water, basified with 30% ammonium hydrate and finally extracted with methylene chloride. The organic layer was dried over sodium sulfate and evaporated to dryness to give 1.1 g of an oily product (90% yield) which was used as such without any further purification.

EXAMPLE 2

Preparation of 2-cyclopropylethanol

Sodium (85 mg; 0.004 mmol) was dissolved in 50 ml of methanol and 8.7 g (0.23 mol) of sodium borohydride were added. A solution of 3.7 g (0.032 mol) of methyl cyclopropylacetate, prepared according to example 1, in 20 ml of methanol was dropped to the mixture under stirring. The reaction was maintained at reflux for 6 hours, then 300 ml of brine were added and the crude extracted with methylene chloride.

The organic layer was dried over sodium sulfate and evaporated to dryness to give 1.52 g (55% yield) of the title compound.

EXAMPLE 3

Preparation of a Compound of Formula (VI): 2-cyclopropylethanal

Oxalyl chloride (1.24 ml; 14.18 mmol) was dissolved in 10 ml of methylene chloride; after cooling to −60° C. a solution of 1.02 g (11.9 mmol) of 2-cyclopropylethanol, prepared according to example 2, in 10 ml of methylene chloride was added dropwise. The mixture was maintained under stirring for 30 minutes at the same temperature, then 8.3 ml (59.5 mmol) of triethylamine were added.

After 2 hours at 0° C. water was added. The mixture was diluted with methylene chloride and washed successively with 1M hydrochloric acid, water, saturated sodium bicarbonate and finally with brine. The organic layer was dried over sodium sulfate and evaporated to dryness to give 0.31 g (30% yield) of the title compound.

EXAMPLE 4

Preparation of a Compound of Formula (II): 2-amino-5-isopropyl-1,3-thiazole

3-Methylbutanaldehyde (2 ml; 18.6 mmol) was dissolved in 15 ml of dioxane.

A solution 2% v/v of bromine in dioxane (47.81 ml; 18.6 mmol) was dropped therein at 0° C. The mixture was maintained at room temperature under stirring for 2 hours, then 2.83 g (37.2 mmol) of thiourea and 10 ml of ethanol were added. After 6 hours at room temperature the solution was evaporated to dryness, the residue was dissolved in methylene chloride and the product extracted with 1M hydrochloric acid; the aqueous layer was made basic by using 30% ammonium hydrate and extracted again with methylene chloride.

The organic phase was dried over sodium sulfate and evaporated under vacuum. The residue was chromatographed on a silica gel column, eluting with cyclohexane-ethylacetate to give 1.1 g (42% yield) of the title compound.

$^1$H-NMR (DMSO-d$^6$) δ ppm: 6.6 (s, 2H, NH$_2$); 6.58 (s, 1H, thiazole CH); 2.9 (m, 1H, C$\underline{H}$Me$_2$); 1.18 (s, 3H, M$\underline{e}$CHMe); 1.17 (s, 3H, MeCHM$\underline{e}$).

By analogous procedures the following compounds can be prepared:

2-amino-5-phenyl-1,3-thiazole; and
2-amino-5-cyclopropyl-1,3-thiazole.

EXAMPLE 5

Preparation of a Compound of Formula (I): N-(5-bromo-1,3-thiazol-2-yl)-N'-phenyl-urea Phenylisocyanate (1.7 ml; 15.6 mmol) was added to a solution of 2-amino-5-bromo-1,3-thiazole hydrobromide (4 g; 15.6 mmol) and triethylamine (2.1 ml; 15.6 mmol) in dichloromethane (70 ml), maintained under magnetic stirring at room temperature. After about 4 days, methanol (7 ml) was added and the reaction mixture was then washed with brine, dried over sodium sulfate and evaporated.

The residue was purified by chromatography on silica gel (dichloromethane and then dichloromethane/methanol= 90:10) to give 1.9 g (52%) of the title compound as a colourless solid (m.p. 166–169° C./dec.).

$^1$H-NMR (CDCl$_3$) δ ppm: 10.50 (bs, 1H, —N$\underline{H}$CONHPh); 8.50 (bs, 1H, —NHCON$\underline{H}$Ph); 7.45 (d, J=7.6 Hz, 2H, o-Ph hydrogens); 7.36 (dd, J=7.3 and 7.6 Hz, 2H, m-Ph hydrogens); 7.29 (s, 1H, thiazole CH); 7.16 (t, J=7.3 Hz, 1H, p-Ph hydrogens).

By analogous procedure, and by starting from the corresponding isocyanate, the following compounds can be prepared:

N-(5-phenyl-1,3-thiazol-2-yl)-N'-phenyl-urea
$^1$H-NMR (DMSO-d$^6$) δ ppm: 10.56 (bs, 1H, —NHCONHPh); 8.99 (bs, 1H, NHCON$\underline{H}$Ph); 7.77 (s, 1H, thiazole CH); 7.6–7.0 (m, 10H, phenyl);

N-(5-bromo-1,3-thiazol-2-yl)-N'-(4-sulfamoyl-phenyl)-urea;

N-(5-isopropyl-1,3-thiazol-2-yl)-N'-(4-sulfamoyl-phenyl)-urea;
m.p.>200° C.
$^1$H-NMR (DMSO-d$^6$) δ ppm: 10.58 (bs, 1H, —N$\underline{H}$CONHPh); 9.38 (bs, 1H NHCON$\underline{H}$Ph); 7.75 (d, 2H, H3 and H5 Ph); 7.61 (d, 2H, H2 and H6 Ph); 7.21 (s, 2H, SO$_2$NH$_2$); 7.02 (s, 1H, thiazole CH); 3.02 (m, 1H, C$\underline{H}$(Me)$_2$); 1.22 (s, 3H, M$\underline{e}$CHMe); 1.21 (s, 3H, MeCHM$\underline{e}$); ESI(+)–MS: m/z 341 (100, (M+H)$^+$).

N-benzoyl-N'-(5-isopropyl-1,3-thiazol-2-yl)urea
m.p.217–219° C.
$^1$H-NMR (400 MHz-DMSO-d$_6$) δ ppm: 1.27 (d, 6H, J=6.8, C$\underline{H_3}$CHC$\underline{H_3}$); 3.11 (m, 1H, CH$_3$C$\underline{H}$CH$_3$); 7.18 (d, 1H, J=0.9, H thiazole); 7.54 (m, 2H, m-phenyl); 7.66 (m, 1H, p-phenyl); 8.00 (m, 2H, o-phenyl); 11.50 (bs, 1H, NH); 11.80 (bs, 1H, NH).
ESI (+)MS: m/z 290 (70, (M+H)$^+$; m/z 169 (100, (MH—C$_6$H$_5$CONH$_2$)$^+$);

N-(5-phenyl-1,3-thiazol-2-yl)-N'-(4-sulfamoyl-phenyl)-urea;

N-(5-cyclopropyl-1,3-thiazol-2-yl)-N'-(4-sulfamoyl-phenyl)-urea;

N-(5-isopropyl-1,3-thiazol-2-yl)-N'-(3-methoxy-phenyl)-urea
m.p. 149–150° C.
$^1$H-NMR (400 MHz-DMSO-d$_6$) δ ppm: 1.23 (d, 6H, J=6.8, C$\underline{H_3}$CHC$\underline{H_3}$); 3.06 (m, 1H, CH$_3$C$\underline{H}$CH$_3$); 3.72 (s, 3H, CH$_3$); 7.02 (s, 1H, H thiazole); 6.57 (dd, 1H, J=8.3, 2.4, H-4'-phenyl); 6.93 (d, 1H, J=8.3, H-6'-phenyl); 7.18 (m, 2H, H-5', H-2'-phenyl); 8.94 (s, 1H, NH); 10.35 (bs, 1H, NH).
ESI (+)MS: m/z 292 (100, (M+H)$^+$);

N-(5-bromo-1,3-thiazol-2-yl)-N'-(3-methoxy-phenyl)-urea
m.p. 190–191° C.
$^1$H-NMR (400 MHz-DMSO-d$_6$) δ ppm: 7.44 (s, 1H, H thiazole); 3.72 (s, 3H, CH$_3$); 6.61 (dd, 1H, J=2.4, 7.8, H-4'-phenyl); 6.94 (dd, 1H, J=2.0, 7.8, H-6'-phenyl); 7.13 (dd, 1H, J=2.0, 2.0, H-2'-phenyl); 7.20 (dd, 1H, J=7.8, 7.8 H-5'-phenyl); 8.95 (s, 1H, NH); 10.80 (s, 1H, NH).
ESI (+)MS: m/z 328 (100, (M+H)$^+$);

N-(5-phenyl-1,3-thiazol-2-yl)-N'-(3-methoxy-phenyl)-urea;

N-(5-cyclopropyl-1,3-thiazol-2-yl)-N'-(3-methoxy-phenyl)-urea;

N-(5-isopropyl-1,3-thiazol-2-yl)-N'-phenyl-urea
$^1$H-NMR (400 MHz-DMSO-d$_6$) δ ppm: 1.24 (d, 6H, J=6.8, CHhd 3CHC$\underline{H_3}$); 3.07 (m, 1H, CH$_3$C$\underline{H}$CH$_3$); 7.03 (m, 2H, H-thiazole+H-4'-phenyl); 7.29 (m, 2H, H-5', H-3'-phenyl); 7.43 (m, 2H, H-2', H-6'-phenyl); 8.91 (s, 1H, NH); 10.30 (bs, 1H, NH).
ESI (+)–MS: m/z 262 (100, (M+H)$^+$);

N-(5-phenyl-1,3-thiazol-2-yl)-N'-phenyl-urea;

N-(5-cyclopropyl-1,3-thiazol-2-yl)-N'-phenyl-urea;

N-(5-isopropyl-1,3-thiazol-2-yl)-N'-(4-chloro-phenyl)-urea
m.p. 191–193° C.
$^1$H-NMR (300 MHz-DMSO-d$_6$) δ ppm: 1.16 (d, 6H, J=6.8, C$\underline{H_3}$CHC$\underline{H_3}$); 3.00 (m, 1H, CH$_3$C$\underline{H}$CH$_3$); 6.95 (d, 1H, J=1.0, H thiazole); 7.40 (d, 2H,J=8.9 m-phenyl); 7.26 (d, 2H, J=8.9 o-phenyl); 9.01 (bs, 1H, NH); 10.40 (bs, 1H, NH).
ESI (+)MS: m/z 296 (100, (M+H)$^+$);

N-(5-bromo-1,3-thiazol-2-yl)-N'-(4-chloro-phenyl)-urea;
N-(5-phenyl-1,3-thiazol-2-yl)-N'-(4-chloro-phenyl)-urea;
N-(5-cyclopropyl-1,3-thiazol-2-yl)-N'-(4-chloro-phenyl)-urea;

N-(5-isopropyl-1,3-thiazol-2-yl)-N'-(3-chloro-phenyl)-urea;

N-(5-bromo-1,3-thiazol-2-yl)-N'-(3-chloro-phenyl)-urea;

N-(5-phenyl-1,3-thiazol-2-yl)-N'-(3-chloro-phenyl)-urea;

N-(5-cyclopropyl-1,3-thiazol-2-yl)-N'-(3-chloro-phenyl)-urea;

N-(5-isopropyl-1,3-thiazol-2-yl)-N'-(2-chloro-phenyl)-urea $^1$H-NMR (400 MHz-DMSO-d$_6$) δ ppm: 1.24 (d, 6H, J=6.8, CHhd 3CHCH$_3$); 3.07 (m, 1H, CH$_3$CHCH$_3$); 7.07 (m, 2H, H-thiazole+H-4'-phenyl); 7.31 (dd, 1H, J=7.8, 7.8, H-5'-phenyl); 7.47 (d, 1H, J=7.8 H-3'-phenyl); 8.14 (d, 1H, J=7.8, H-6'-phenyl); 8.80 (bs, 1H, NH); 11.01 (bs, 1H, NH).

ESI (+)MS: m/z 296 (100, (M+H)$^+$);

N-(5-bromo-1,3-thiazol-2-yl)-N'-(2-chloro-phenyl)-urea m.p.210–212° C.

$^1$H-NMR (300 MHz-DMSO-d$_6$) δ ppm: 7.29 (s, 1H, H-thiazole); 7.02 (ddd, 1H, J=1.6, 7.6, 7.6, H-4'-phenyl); 7.25 (ddd, 1H, J=1.6, 7.6, 7.6, H-5'-phenyl); 7.41 (dd, 1H, J=1.6, 7.6, H-3'-phenyl); 8.03 (dd, 1H, J=1.6, 7.6, H-6'-phenyl); 8.58 (s, 1H, NH); 11.31 (bs, 1H, NH).

ESI (+)MS: m/z 332 (100, (M+H)$^+$);

N-(5-phenyl-1,3-thiazol-2-yl)-N'-(2-chloro-phenyl)-urea;

N-(5-cyclopropyl-1,3-thiazol-2-yl)-N'-(2-chloro-phenyl)-urea;

N-(5-isopropyl-1,3-thiazol-2-yl)-N'-(4-methoxy-phenyl)-urea;

N-(5-bromo-1,3-thiazol-2-yl)-N'-(4-methoxy-phenyl)-urea;

N-(5-phenyl-1,3-thiazol-2-yl)-N'-(4-methoxy-phenyl)-urea;

N-(5-cyclopropyl-1,3-thiazol-2-yl)-N'-(4-methoxy-phenyl)-urea;

N-(5-bromo-1,3-thiazol-2-yl)-N'-(4-hydroxy-phenyl)-urea;

N-(5-phenyl-1,3-thiazol-2-yl)-N'-(4-hydroxy-phenyl)-urea;

N-(5-cyclopropyl-1,3-thiazol-2-yl)-N'-(4-hydroxy-phenyl)-area;

N-(5-bromo-1,3-thiazol-2-yl)-N'-(3-hydroxy-phenyl)-urea;

N-(5-phenyl-1,3-thiazol-2-yl)-N'-(3-hydroxy-phenyl)-urea;

N-(5-cyclopropyl-1,3-thiazol-2-yl)-N'-(3-hydroxy-phenyl)-urea;

N-(5-isopropyl-1,3-thiazol-2-yl)-N'-(2-methoxy-phenyl)-urea;

m.p. 184–185° C.;

$^1$H-NMR (400 MHz-DMSO-d$_6$) δ ppm: 1.23 (d, 6H, J=6.7, CH$_3$CHCH$_3$); 3.07 (m, 1H, CH$_3$CHCH$_3$); 3.85 (s, 3H, OCH$_3$); 6.92 (m, 1H, H-phenyl); 7.01 (m, 3H, H-phenyl+H-thiazole); 8.07 (d, 1H, J=8.3, H-6'-phenyl); 8.80 (bs, 1H, NH); 10.82 (s, 1H, NH).

ESI(+)–MS: m/z 292 (100, (M+H)$^+$);

N-(5-bromo-1,3-thiazol-2-yl)-N'-(2-methoxy-phenyl)-urea m.p. 218–220° C.

$^1$H-NMR (300 MHz-DMSO-d$_6$) δ ppm: 3.79 (s, 3H, CH$_3$O); 6.90–7.98 (2m, 4H, phenyl); 7.36 (s, 1H, H thiazole); 8.57 (s, 1H, NH); 11.13 (bs, 1H, NH).

ESI (+)MS: m/z 328 (100, (M+H)$^+$

N-(5-phenyl-1,3-thiazol-2-yl)-N'-(2-methoxy-phenyl)-urea;

N-(5-cyclopropyl-1,3-thiazol-2-yl)-N'-(2-methoxy-phenyl)-urea;

N-(5-bromo-1,3-thiazol-2-yl)-N'-(2-hydroxy-phenyl)-urea;

N-(5-phenyl-1,3-thiazol-2-yl)-N'-(2-hydroxy-phenyl)-urea;

N-(5-cyclopropyl-1,3-thiazol-2-yl)-N'-(2-hydroxy-phenyl)-urea;

N-(5-isopropyl-1,3-thiazol-2-yl)-N'-(4-nitro-phenyl)-urea;

$^1$H-NMR (400 MHz-DMSO-d$_6$) δ ppm: 1.23 (d, 6H, J=6.8, CH$_3$CHCH$_3$); 3.14 (m, 1H, CH$_3$CHCH$_3$); 7.04 (s, 1H, H-thiazole); 7.74 (d, 2H, J=9.3, H-2', H-6'-phenyl); 8.18 (d, 2H, J=9.3, H-3', H-5'-phenyl); 9.65 (bs, 1H, NH); 11 (bs, 1H, NH).

ESI(+)–MS: m/z 307 (100, (M+H)$^+$);

N-(5-bromo-1,3-thiazol-2-yl)-N'-(4-nitro-phenyl)-urea;

N-(5-phenyl-1,3-thiazol-2-yl)-N'-(4-nitro-phenyl)-urea;

N-(5-cyclopropyl-1,3-thiazol-2-yl)-N'-(4-nitro-phenyl)-urea;

N-(5-isopropyl-1,3-thiazol-2-yl)-N'-(3-nitro-phenyl)-urea;

m.p. 220–222° C.

$^1$H-NMR (400 MHz-DMSO-d$_6$) δ ppm: 1.24 (d, 6H, J=6.9, CH$_3$CHCH$_3$); 3.05 (m, 1H, CH$_3$CHCH$_3$); 7.04 (s, 1H, H thiazole); 7.56 (dd, 1H, J=8.2, 8.2, H-5-phenyl); 7.77 (d, 1H, J=8.2, H-6'-phenyl);7.83 (dd, 1H, J=8.2, 1.5, H-4'-phenyl); 8.58 (d, 1H, J=1.5, H-2'-phenyl); 9.45 (s, 1H, NH); 10.60 (bs, 1H, NH).

ESI (+)–MS: m/z 307 (100, (M+H)$^+$);

N-(5-bromo-1,3-thiazol-2-yl)-N'-(3-nitro-phenyl)-urea;

N-(5-phenyl-1,3-thiazol-2-yl)-N'-(3-nitro-phenyl)-urea;

N-(5-cyclopropyl-1,3-thiazol-2-yl)-N'-(3-nitro-phenyl)-urea;

N-(5-isopropyl-1,3-thiazol-2-yl)-N'-benzyl-urea $^1$H-NMR (400 MHz-DMSO-d$_6$) δ ppm: 1.21 (d, 6H, J=6.8, CH$_3$CHCH$_3$); 3.03 (m, 1H, CH$_3$CHCH$_3$); 4.31 (d, 2H, J=6.35, CH$_2$); 6.96 (m, 1H, NH—CH$_2$); 7.27 (m, 5H, phenyl).

ESI (+)MS: m/z 276 (100, (M+H)$^+$);

N-(5-bromo-1,3-thiazol-2-yl)-N'-benzyl-urea;

N-(5-phenyl-1,3-thiazol-2-yl)-N'-benzyl-urea;

N-(5-cyclopropyl-1,3-thiazol-2-yl)-N'-benzyl-urea;

N-(5-isopropyl-1,3-thiazol-2-yl)-N'-(pyrid-3-yl)-urea;

N-(5-bromo-1,3-thiazol-2-yl)-N'-(pyrid-3-yl)-urea;

N-(5-phenyl-1,3-thiazol-2-yl)-N'-(pyrid-3-yl)-urea;

N-(5-cyclopropyl-1,3-thiazol-2-yl)-N'-(pyrid-3-yl)-urea;

N-(5-bromo-1,3-thiazol-2-yl)-N'-(pyrid-4-yl)-urea;

N-(5-isopropyl-1,3-thiazol-2-yl)-N'-(pyrid-4-yl)-urea;

N-(5-phenyl-1,3-thiazol-2-yl)-N'-(pyrid-4-yl)-urea;

N-(5-cyclopropyl-1,3-thiazol-2-yl)-N'-(pyrid-4-yl)-urea;

N-(5-isopropyl-1,3-thiazol-2-yl)-N'-(pyrid-2-yl)-urea;

N-(5-bromo-1,3-thiazol-2-yl)-N'-(pyrid-2-yl)-urea;

N-(5-phenyl-1,3-thiazol-2-yl)-N'-(pyrid-2-yl)-urea;

N-(5-cyclopropyl-1,3-thiazol-2-yl)-N'-(pyrid-2-yl)-urea;

N-(5-isopropyl-1,3-thiazol-2-yl)-N'-(benzothiophen-2-yl)-urea;

N-(5-bromo-1,3-thiazol-2-yl)-N'-(benzothiophen-2-yl)-urea;

N-(5-phenyl-1,3-thiazol-2-yl)-N'-(benzothiophen-2-yl)-urea; and

N-(5-cyclopropyl-1,3-thiazol-2-yl)-N'-(benzothiophen-2-yl)-urea;

EXAMPLE 6

Preparation of a Compound of Formula (VI): 4-nitrophenyl-5-isopropyl-1,3-thiazol-2-ylcarbamate To a solution of 4 g (28.13 mmol) of 5-isopropyl-2-amino-1,3-thiazole in 30 ml of anhydrous dichloromethane 5.7 g (28.13 mmol) of 4-nitrophenyl chloroformate were added dropwise at 0° C. under nitrogen. Then 2.3 ml of pyridine were added. The mixture was maintained at room temperature under stirring overnight and then filtered, giving 6.96 g (80% yield) of the title compound as a white solid.

m.p. 157–159° C.

$^1$H-NMR (400 MHz-DMSO-d$_6$) δ ppm: 1.23 (d, 6H, J=6.8, C$\underline{H}_3$CHC$\underline{H}_3$); 3.06 (m, 1H, CH$_3$C$\underline{H}$CH$_3$); 7.05 (s, 1H, H thiazole); 6.91 (d, 2H, J=9.2, H-3',5'-phenyl); 8.10 (d, 2H, J=9.2, H-2',6'-phenyl); 11.00 (bs, 1H, NH).

EI-MS: m/z 307 (0.5, M$^+$); m/z 168 ((CH3)$_2$—CH-thiazole-NCO)$^+$; m/z 153 (100, (CH$_3$—CH-thiazole-NCO)$^+$); m/z 139 (45, (OH—C$_6$H$_8$—NO$_2$)$^+$).

EXAMPLE 7

Preparation of a Compound of Formula (I): N-(5-isopropyl-1,3-thiazol-2-yl)-N'-(3-iodophenyl)urea 1 g (3.25 mmol) of 4-nitrophenyl-5-isopropyl-1,3-thiazol-2-ylcarbamate and 0.39 ml (3.25 mmol) of 3-iodoaniline were suspended under argon in 25 ml of acetonitrile. After 2 hours at 70° C. the resulting solution was cooled, giving rise 0.923 g of the title compound, recrystallized from a mixture of diethylether/pentane 1/1.

m.p. 160–162° C.

$^1$H-NMR (300 MHz-DMSO-d$_6$) δ ppm: 1.23 (d, 6H, J=6.8, C$\underline{H}_3$CHC$\underline{H}_3$); 3.05 (m, 1H, CH$_3$C$\underline{H}$CH$_3$); 7.03 (d, 1H, J=0.8, H thiazole); 7.07 (t, 1H, J=8.0, H-5'-phenyl); 7.35 (m, 2H, H-4',6'-phenyl); 8.00 (t, 1H, J=1.8, 1.8, H-2'-phenyl); 9.06 (bs, 1H, NH); 10.50 (bs, 1H, NH).

ESI (+)-MS: m/z 388 (100, (M+H)$^+$).

By analogous procedure but employing 2-[(2-propynylamino)methyl]benzenesulfonamide, 2-{[{[(5-isopropyl-1,3-thiazol-2-yl)amino]carbonyl}(2-propynyl)amino]methyl}benzenesulfonamide can be prepared m.p. 90–92° C.

$^1$H-NMR (400 MHz-DMSO) δ ppm: 1.19 (d, 6H, J=6.8, CH$_3$CHC$\underline{H}_3$); 2.93 (m, 1H, C$\underline{H}$≡C—); 3.13 (m, 1H, CH$_3$C$\underline{H}$CH$_3$); 4.18, 5.08 (2m, 4H, C$\underline{H}_2$Ph+C$\underline{H}_2$C≡C); 6.89 (m, 1H, H-thiazole); 7.22 (m, 1H, H-3'-phenyl); 7.41, 7.53 (2m, 2H, H-5', H-4'-phenyl); 7.86 (m, 1H, H-6'-phenyl); 11.90 (bs, 1H, NH).

ESI(+)-MS: m/z 415 (100, (M+Na)$^+$); m/z 393 (50, (M+H)$^+$.

By analogous procedure but employing 1H-benzimidazol-6-amine, N-(1H-benzimidazol-5-yl)N'-(5-iosopropyl-1,3-thiazol-2-yl)urea can be obtained.

$^1$H-NMR (400 MHz-DMSO-d$_6$) δ ppm: 1.27 (d, 6H, J=6.8, C$\underline{H}_3$CHC$\underline{H}_3$); 3.09 (m, 1H, CH$_3$C$\underline{H}$CH$_3$); 7.01 (s, 1H, H-thiazole); 7.13 (d, 1H, H-6'-benzimidazole); 7.49 (d, 1H, H-7'-benzimidazole); 7.81 (s, 1H, H-4'-benzimidazole); 8.03 (s, 1H, H-2'-benzimidazole).

ESI(+)-MS: m/z 302 (100, (M+H)$^+$).

By analogous procedure but employing 1H-indole-6-amine, N-(1H-indol-6-yl)-N'-(5-isopropyl-1,3-thiazol-2-yl) urea can be prepared.

$^1$H-NMR (400 MHz-DMSO-d$_6$) δ ppm: 1.24 (d, 6H, J=6.8, C$\underline{H}_3$CHC$\underline{H}_3$); 3.06 (m, 1H, CH$_3$C$\underline{H}$CH$_3$); 7.03 (bs, 1H, H thiazole); 6.33 (m, 1H, H-3'-indole); 6.84 (d, 1H, J=8.3, H-5'-indole); 7.23 (t, 1H, J=2.4, 2.4, H-2'-indole); 7.42 (d, 1H, J=8.3, H-4'-indole); 7.77 (s, 1H, H-7'-indole); 8.82 (s, 1H, NH); 10.18 (bs, 1H, NH); 10.95 (s, 1H, NH-indole).

ESI (+)-MS: m/z 301 (100, (M+H)$^+$).

By analogous procedure but employing 1H-indole-5-amine, N-(1H-indol-5-yl)-N'-(5-isopropyl-1,3-thiazol-2-yl) urea can be prepared.

$^1$H-NMR (400 MHz-DMSO-d$_6$) δ ppm: 1.24 (d, 6H, J=6.8, C$\underline{H}_3$CHC$\underline{H}_3$); 3.06 (m, 1H, CH$_3$C$\underline{H}$CH$_3$); 7.02 (s, 1H, H thiazole); 6.35 (m, 1H, H-3'-indole); 7.05 (dd, 1H, J=2.0, J=8.5, H-6'-indole); 7.30 (m, 2H, H-2', H-7'-indole); 7.67 (d, 1H, J=2.0, H-4'-indole); 8.68 (s, 1H, NH); 10.15 (s, 1H, NH); 10.98 (s, 1H, NH-indole).

ESI (+)-MS: m/z 301 (100, (M+H)$^+$).

By analogous procedure but employing imidazo[1,2-a]pyridin-2-ylmethanamide, N-(imidazo[1,2-a]pyridin-2-ylmethyl)-N'-(5-isopropyl-1,3-thiazol-2-yl)urea can be prepared.

$^1$H-NMR (400 MHz-DMSO-d$_6$) δ ppm: 1.21 (d, 6H, J=6.8, C$\underline{H}_3$CHC$\underline{H}_3$); 3.04 (m, 1H, CH$_3$C$\underline{H}$CH$_3$); 4.40 (d, 2H, J=5.6, C$\underline{H}_2$);6.96 (d, 1H, J=1.2, H thiazole); 6.84 (dt, 1H, J=2.2, 6.8, H-6'-imidazopyridine); 7.20 (m, 1H, H-5'-imidazopyridine); 7.47 (m, 1H, H-7'-imidazopyridine); 7.78 (s, 1H, H-3'-imidazopyridine); 8.49 (m, 1H, H-4'-imidazopyridine); 7.01 (t, 1H, J=5.4, N$\underline{H}$—CH$_2$); 10.23 (bs, 1H, NH—CO).

ESI(+)-MS: m/z 316 (100, (M+H)$^+$); m/z 338 (85, (M+Na)$^+$).

By analogous procedure but employing 1-methyl-2-[(2-aminophenoxy)methyl]1H-imidazole, N-(5-isopropyl-1,3-thiazol-2-yl)-N'-{2-[(1-methyl-1H-imidazol-2-yl)methoxy]phenyl}urea can be prepared.

$^1$H-NMR (300 MHz-DMSO-d$_6$) δ ppm: 1.23 (d, 6H, J=6.8, C$\underline{H}_3$CHC$\underline{H}_3$); 3.05 (m, 1H, CH$_3$C$\underline{H}$CH$_3$); 3.70 (s, 3H, N—CH$_3$); 5.21 (s, 2H, C$\underline{H}_2$);6.92 (bs, 1H, H thiazole); 6.90–8.20 (m, 6H, imidazole+phenyl); 8.10 (bs, 1H, NH); 10.96 (s, 1H, NH).

ESI(+)-MS: m/z 372 (95, (M+H)$^+$); m/z 410 (100, (M+K)$^+$).

By analogous procedure but employing 2-(2-aminophenoxy)acetamide, N-(5-isopropyl-1,3thiazol-2-yl)-N'-(2-phenoxyacetamido)urea can be prepared.

$^1$H-NMR (400 MHz-DMSO-d$_6$) δ ppm: 1.24 (d, 6H, J=7.0, C$\underline{H}_3$CHC$\underline{H}_3$); 3.07 (m, 1H, CH$_3$C$\underline{H}$CH$_3$); 4.50 (s, 2H, CH$_2$); 7.05 (d, 1H, J=1.0, H thiazole); 6.50–7.00 (m, 3H, phenyl); 8.10 (m, 1H, phenyl), 7.55 (s, 2H, NH$_2$), 8.67 (bs, 1H, NH); 10.86 (s, 1H, NH).

ESI(+)-MS: m/z 335 (50, (M+H)$^+$); .m/z 373 (100, (M+K)$^+$).

By analogous procedure but employing (2S)-2-amino-2-phenylethanamide, N-(5-isopropyl-1,3-thiazol-2-yl)-N'-[(S)-phenylglicinamido]urea can be prepared.

$^1$H-NMR (300 MHz-DMSO-d$_6$) δ ppm: 1.19 (d, 6H, J=6.8, C$\underline{H}_3$CHC$\underline{H}_3$); 3.01 (m, 1H, CH$_3$C$\underline{H}$CH$_3$); 5.26 (d, 1H, J=7.7 C$\underline{H}$); 6.95 (s, 1H, H-thiazole); 7.20–7.60 (m, 6H, N$\underline{H}$—CH+phenyl); 7.20–7.80 (s, 2H, NH$_2$), 10.26 (bs, 1H, NH).

ESI(+)-MS: m/z 319 (25, (M+H)$^+$); .m/z 357 (100, (M+K)$^+$);

By analogous procedure but employing (2R)-2-amino-2-phenylethanamide, N-(5-isopropyl-1,3-thiazol-2-yl)-N'-[(R)-phenylglicinamido]urea can be prepared.

$^1$H-NMR (400 MHz-DMSO-d$_6$) δ ppm: 1.19 (d, 6H, J=7.0, C$\underline{H}_3$CHC$\underline{H}_3$); 3.01 (m, 1H, CH$_3$C$\underline{H}$CH$_3$); 5.26 (d, 1H, J=7.6 C$\underline{H}$); 6.95 (d, 1H, J=1.3, H thiazole); 7.20–7.50 (m, 6H, N$\underline{H}$—CH+phenyl); 7.21–7.79 (s, 2H, NH$_2$), 10.20 (bs, 1H, NH).

ESI(+)-MS: m/z 319 (100, (M+H)$^+$); .m/z 357 (65, (M+K)$^+$).

By analogous procedure but employing 2-aminophenol, N-(2-hydroxyphenyl)-N'-(5-isopropyl-1,3-thiazol-2-yl)urea can be prepared.

m.p. 204–206° C.

$^1$H-NMR (400 MHz-DMSO-d$_6$) δ ppm: 1.23 (d, 6H, J=6.8, C$\underline{H}_3$CHC$\underline{H}_3$); 3.06 (m, 1H, CH$_3$C$\underline{H}$CH$_3$); 7.02 (s, 1H, H-thiazole); 6.74 (m, 1H, H-5'-phenyl); 6.82 (m, 2H, H-3', H-4'-phenyl); 7.98 (d, 1H, J=7.6, H-6'-phenyl); 8.60 (bs, 1H, NH); 10.0 (bs, 1H, NH); 10.80 (bs, 1H, OH).

ESI(+)–MS: m/z 278 (100, (M+H)$^+$).

By analogous procedure but employing 3-aminophenol, N-(3-hydroxyphenyl)-N'-(5-isopropyl-1,3-thiazol-2-yl)urea can be prepared.

m.p.185–187° C.

$^1$H-NMR (400 MHz-DMSO-d$_6$) δ ppm: 1.23 (d, 6H, J=6.8, C$\underline{H}_3$CHC$\underline{H}_3$); 3.05 (m, 1H, CH$_3$C$\underline{H}$CH$_3$); 7.03 (m, 3H, H-thiazole+H-2',H-5'-phenyl); 6.39 (d, 2H, J=8.0, H-4'-phenyl); 6.77 (d, 2H, J=8.0, H-6'-phenyl); 8.81 (s, 1H, NH); 9.37 (s, 1H, NH).

ESI(+)–MS: m/z 278 (100, (M+H)$^+$).

By analogous procedure but employing 4-aminophenol, N-(4-hydroxyphenyl)-N'-(5-isopropyl-1,3-thiazol-2-yl)urea can be prepared.

m.p.130–132° C.

$^1$H-NMR (400 MHz-DMSO-d$_6$) δ ppm: 1.23 (d, 6H, J=6.8, C$\underline{H}_3$CHC$\underline{H}_3$); 3.05 (m, 1H, CH$_3$C$\underline{H}$CH$_3$); 7.00 (s, 1H, H-thiazole); 6.68 (d, 2H, J=8.8, H-3', H-5'-phenyl); 7.21 (d, 2H, J=8.8, H-2',H-6'-phenyl); 8.60 (s, 1H, NH); 9.14 (s, 1H, NH); 10.18 (bs, 1H, OH).

ESI(+)–MS: m/z 278 (100, (M+H)$^+$).

By analogous procedure but employing (2R)-2-amino-2-phenyl-1-ethanol, N-[(1S)-2-hydroxy-1-phenylethyl]-N'-(5-isopropyl-1,3-thiazol-2-yl)urea can be prepared.

$^1$H-NMR (400 MHz-DMSO-d$_6$) δ ppm: 1.20 (d, 6H, J=7.0, C$\underline{H}_3$CHC$\underline{H}_3$); 3.01 (m, 1H, CH$_3$C$\underline{H}$CH$_3$); 3.60 (s, 2H, CH$_2$); 4.73 (m, 1H, CH); 5.00 (t, 1H, J=5.1, 5.1, OH); 6.95 (d, 1H, J=1.1, H thiazole); 7.10–7.40 (m, 6H, N$\underline{H}$—CH+phenyl); 10.15 (s, 1H, NH).

ESI(+)–MS: m/z 306 (100, (M+H)$^+$).

By analogous procedure but employing (2S)-2-amino-2-phenyl-1-ethanol, N-[(1R)-2-hydroxy-1-phenylethyl]-N'-(5-isopropyl-1,3-thiazol-2-yl)urea can be prepared.

$^1$H-NMR (400 MHz-DMSO-d$_6$) δ ppm: 1.19 (d, 6H, J=6.9, C$\underline{H}_3$CHC$\underline{H}_3$); 3.01 (m, 1H, CH$_3$C$\underline{H}$CH$_3$); 3.59 (m, 2H, CH$_2$); 4.73 (m, 1H, CH); 5.02 (t, 1H, J=5.1, 5.1, OH); 6.95 (d, 1H, J=0.7, H thiazole); 7.20–7.40 (m, 6H, N$\underline{H}$—CH+phenyl); 10.17 (s, 1H, NH).

ESI(+)–MS: m/z 306 (100, (M+H)$^+$).

EXAMPLE 8

Preparation of a Compound of Formula (I): N-[3-(3-hydroxy-1-butynyl)phenyl]-N'-(5-isopropyl-1,3-thiazol-2-yl)urea To a solution of 0.2 g (0.56 mmol) of N-(5-isopropyl-1,3-thiazol-2-yl)-N'-(3-iodophenyl)urea in 3 ml of anhydrous N,N-dimethylformamide 0.6 ml of tetramethylguanidine, 0.088 ml (1.126 mmol) of D,L-1-butyn-3-ol, 19 mg (0.027 mmol) of bis(triphenylphosphine)palladium(II) dihydrochloride and 5.8 mg (0.03 mmol) of rameous iodide under argon were added successively. After 5 hours water was added and the mixture extracted with ethylacetate. The organic layer was washed with brine, dried over sodium sulfate and evaporated, giving 0.116 g of the title compound as a yellowish solid.

m.p. 71–73° C.

$^1$H-NMR (400 MHz-DMSO-d$_6$) δ ppm: 1.24 (d, 6H, J=6.9, C$\underline{H}_3$CHC$\underline{H}_3$); 3.06 (m, 1H, CH$_3$C$\underline{H}$CH$_3$); 1.37 (d, 3H, J=6.6, CH$_3$);4.57 (m, 1H, CH); 5.43 (d, 1H, J=5.1, OH); 7.03 (s, 1H, H thiazole); 7.02 (d, 1H, J=8.0, H-4'-phenyl) ;7.27 (t, 1H, J=8.0, 8.0, H-5'-phenyl); 7.34 (d, 1H, J=8.0, H-6'-phenyl); 7.65 (s, 1H, H-2'-phenyl); 8.02 (s, 1H, NH); 10.40 (bs, 1H, NH).

ESI(+)–MS: m/z 330 (100, (M+H)$^+$).

By analogous procedure and by starting from N,N-dimethyl-2-propyl-1-amine, N-{3-[3-(dimethylamino)-1-propynyl]phenyl}-N'-(5-isopropyl-1,3-thiazol-2-yl)urea can be prepared;

$^1$H-NMR (400 MHz-DMSO-d$_6$) δ ppm: 1.23 (d, 6H, J=6.8, C$\underline{H}_3$CHC$\underline{H}_3$); 3.05 (m, 1H, CH$_3$C$\underline{H}$CH$_3$); 2.23 (s, 6H, N(CH$_3$)$_2$); 3.44 (s, 2H, CH$_2$); 7.03 (s, 1H, H-thiazole); 7.05 (d, 1H, J=7.8, H-4'-phenyl);7.27 (t, 1H, J=7.8,7.8, H-5'-phenyl); 7.36 (d, 1H, J=7.8, H-6'-phenyl); 7.64 (s, 1H, H-2'-phenyl); 9.04 (bs, 1H, NH); 10.45 (bs, 1H, NH).

ESI(+)–MS: m/z 343 (100, (M+H)$^+$).

By analogous procedure and by starting from 3-methoxy-1-propyne, N-[3-(3-methoxy-1-propynyl)phenyl]-N'-(5-isopropyl-1,3-thiazol-2-yl)urea can be prepared;

$^1$H-NMR (400 MHz-DMSO-d$_6$) δ ppm: 1.23 (d, 6H, J=6.8, C$\underline{H}_3$CHC$\underline{H}_3$); 3.05 (m, 1H, CH$_3$C$\underline{H}$CH$_3$); 3.32 (s, 3H, CH$_3$); 4.31 (s, 2H, CH$_2$); 7.03 (s, 1H, H-thiazole); 7.08 (d, 1H, J=8.3, H-4'-phenyl);7.29 (t, 1H, J=8.3,8.3, H-5'-phenyl); 7.39 (d, 1H, J=8.3, H-6'-phenyl); 7.67 (s, 1H, H-2'-phenyl); 9.03 (s, 1H, NH); 10.40 (bs, 1H, NH).

ESI(+)–MS: m/z 330 (100, (M+H)$^+$).

EXAMPLE 9

Preparation of a Compound of Formula (I): N-(5-isopropyl-1,3-thiazol-2-yl)-N'-(3-aminophenyl)urea A mixture of 1.55 g (5.05 mmol) of (5-isopropyl-1,3-thiazol-2-yl)-N'-(3-nitrophenyl)urea prepared as described in example 5 and 0.98 g ((17.7 mmol) of iron dust with 2.02 ml (35.35 mmol) of glacial acetic acid in 50 ml of ethanol was stirred at reflux under argon atmosphere. After 5 hours 1.5 l of water was added and the product extracted with ethylacetate. The organic layer was washed with brine, dried over sodium sulfate and evaporated. The residue was finally purified by chromatography on a silica gel column (chloroform/methanol 47/3) giving 0.84 g of the title compound as a white solid.

m.p. 113–115° C.

$^1$H-NMR (400 MHz-DMSO-d$_6$) δ ppm: 1.23 (d, 6H, J=6.8, C$\underline{H}_3$CHC$\underline{H}_3$); 3.05 (m, 1H, CH$_3$C$\underline{H}$CH$_3$); 5.07 (s, 2H, NH$_2$); 7.02 (s, 1H, H-thiazole); 6.20 (dd, 1H, J=2.0, 7.8, H-4'-phenyl);6.52 (dd, 1H, J=1.5, 8.3, H-6'-phenyl); 6.76 (bs, 1H, H-2'-phenyl); 6.89 (t, 1H, J=8.3, 8.3, H5'-phenyl); 8.61 (s, 1H, NH); 10.13 (bs, 1H, NH).

ESI(+)–MS: m/z 277 (100, (M+H)$^+$).

By analogous procedure and by starting respectively from N-(5-isopropyl-1,3-thiazol-2-yl)-N'-(2-nitrophenyl)urea and N-(5-isopropyl-1,3-thiazol-2-yl)-N'-(4-nitrophenyl)urea, the following compounds can be prepared:

N-(5-isopropyl-1,3-thiazol-2-yl)-N'-(2-aminophenyl)urea;

N-(5-isopropyl-1,3-thiazol-2-yl)-N'-(4-aminophenyl)urea.

$^1$H-NMR (400 MHz-DMSO-d$_6$) δ ppm: 1.22 (d, 6H, J=6.8, C$\underline{H}_3$CHC$\underline{H}_3$); 3.04 (m, 1H, CH$_3$C$\underline{H}$CH$_3$); 4.83 (s, 2H, NH$_2$); 6.99 (s, 1H, H-thiazole); 6.50 (d, 2H, J=8.7, H-3', H-5'-phenyl); 7.05 (d, 2H, J=8.7, H-2', H-6'-phenyl); 8.42 (s, 1H , NH); 10.09 (bs, 1H, NH).

ESI(+)–MS: m/z 277 (100, (M+H)$^+$).

Again by analogous procedure, and by starting respectively from 6-nitro-1H-indole and from 6-nitro-1H-benzimidazole, 1H-indol-6-amine and 1H-benzimidazol-6-amine can be prepared.

EXAMPLE 10

Preparation of a Compound of Formula (I): N-[4-({[(5-isopropyl-1,3-thiazol-2-yl)amino]phenyl] methanesulfonamide 0.2 g (0.724 mmol) of N-(5-isopropyl-1,3-thiazol-2-yl)-N'-(3-aminophenyl)urea were dissolved in 10 ml of absolute ethanol and 0.2 g (1.95 mmol) of potassium hydrogen carbonate and 124.3 mg (1.0855 mmol) of methanesulfonylchloride were added successively. The mixture was maintained at 80° C. under argon for 7 hours and then evaporated. The residue was partitioned between water and dichloromethane. The organic layer was then dried over sodium sulfate and afforded, after concentration and cooling, 104 mg of the title compound as a white solid.

m.p. 246–248° C.

$^1$H-NMR (400 MHz-DMSO-$d_6$) δ ppm: 1.23 (d, 6H, J=6.8, C$\underline{H}_3$CHC$\underline{H}_3$); 3.06 (m, 1H, CH$_3$C$\underline{H}$CH$_3$); 2.97 (s, 3H, CH$_3$); 7.03 (s, 1H, H-thiazole); 6.84 (d, 1H, J=6.8, H-6'-phenyl); 7.19 (m, 2H, H-4', H-5'-phenyl); 7.39 (s, 1H, H-2'-phenyl); 9.00 (s, 1H, NH); 9.72 (bs, 1H, NH); 10.18 (bs, 1H, NHSO$_2$).

ESI(+)–MS: m/z 355 (100, (M+H)$^+$).

EXAMPLE 11

Preparation of a Compound of Formula (I)

2-[3-({[5-isopropyl-1,3-thiazol-2-yl)amino]carbonyl}amino)anilino]acetamide

To a solution of 0.2 g (0.724 mmol) of N-(5-isopropyl-1,3-thiazol-2-yl)-N'-(3-aminophenyl)urea in 2 ml of N,N-dimethylformamide, 100 mg (0.724 mmol) of 2-bromoacetamide and 108.6 mg (1.95 mmol) of potassium hydrogencarbonate were added successively. The mixture was maintained 8 hours at 40° C. under argon, then poured into water and extracted with dichloromethane. The organic layer was then washed with brine, dried over sodium sulfate and concentrated to give, after cooling, 160 mg of the title compound.

m.p. 133–135° C.

$^1$H-NMR (400 MHz-DMSO-$d_6$) δ ppm: 1.23 (d, 6H, J=6.8, C$\underline{H}_3$CHC$\underline{H}_3$); 3.06 (m, 1H, CH$_3$C$\underline{H}$CH$_3$); 3.54 (d, 2H, J=5.4, CH$_2$); 7.02 (s, 1H, H-thiazole); 5.88 (m, 1H, N$\underline{H}$—CH$_2$); 6.21 (d, 1H, J=7.8, H-4'-phenyl); 6.65 (d, 1H, J=7.8, H-6'-phenyl); 6.69 (s, 1H, H-2'-phenyl); 6.98 (t, 1H, J=7.8, 7.8, H-5'-phenyl); 8.71 (s, 1H, NH); 10.11 (s, 1H, NH); 7.08, 7.29 (s, 2H, NH$_2$).

ESI(+)–MS: m/z 334 (100, (M+H)$^+$).

EXAMPLE 12

Preparation of (2R)-2-amino-2-phenylethanamide 3.025 g (15 mmol) of (2R)-2-amino-2-phenylethanoate hydrochloride were suspended in 45 ml of dioxane and 45 ml of aqueous ammonium hydrate were added. After 8 hours at room temperature under stirring the solvent was evaporated and the residue redissolved with chloroform and washed with water. The organic layer was concentrated to afford 1.7 g of the title compound as a white solid.

By analogous procedure and by starting from (2S)-2-amino-2-phenylethanoate, (2S)-2-amino-2-phenylethanamide can be prepared.

EXAMPLE 13

Preparation of 1-methyl-2-[(2-nitrophenoxy)methyl]-1H-imidazole

A solution of 1.92 g (11.97 mmol) of o-nitrophenol sodium salt, 3.8 g (35.9 mmol) of sodium carbonate, 2 g (11.97 mmol) of 1-methyl-2-chloromethylimidazole hydrochloride in 30 ml of N,N-dimethylformamide were heated at 50° C. for 2 hours. The mixture was then poured into water and extracted with ethylacetate. The organic layer was washed with brine, dried over sodium sulfate and evaporated, affording 1.17 g of the title compound, recrystallized from diethylether.

m.p. 172–174° C.

$^1$H-NMR (400 MHz-DMSO-$d_6$) δ ppm: 3.67 (s, 3H, CH$_3$); 5.34 (s, 2H, OCH$_2$); 6.86 (s, 1H, H-4-imidazole); 7.13 (m, 1H, H-6-phenyl); 7.19 (s, 1H, H-5-imidazole); 7.60 (m, 1H, H-3 phenyl).

ESI(+)MS: m/z 234 (100, (M+H)$^+$).

By analogous procedure and by starting from 2-chloroacetamide, 2-(2-nitrophenoxy)acetamide can be prepared.

m.p. 190–192° C.

$^1$H-NMR (400 MHz-DMSO-$d_6$) δ ppm: 4.65 (s, 2H, CH$_2$); 7.14 (ddd, 1H, J=1.0, 7.5, 7.9, H-4); 7.22 (dd, 1H, J=1.0, 8.7); H-6); 7.32, 7.47 (2bs, 2H, CONH$_2$); 7.64 (ddd, J=1.5, 7.5, 8.7, H-5); 7.90 (dd, 1H, J=1.5, 7.9, H-3).

ESI(+)MS: m/z 197 (100, (M+H)$^+$).

EXAMPLE 14

Preparation of 1-methyl-2-[(2-aminophenoxy)methyl]-1H-imidazole

A solution of 1.13 g of 1-methyl-2-[(2-nitrophenoxy)methyl]-1H-imidazole in 70 ml of methanol with 0.14 g of palladium on charcoal 10% was hydrogenated at 50 psi for 6 hours at room temperature. The catalyst was then separated by filtration and the solvent evaporated. The residue was finally purified by chromatography on a silica gel column (eluent: chloroform-methanol 48/2) giving rise 0.856 g of the title compound as a red oil.

$^1$H-NMR (400 MHz-DMSO-$d_6$) δ ppm: 3.72 (s, 3H, CH$_3$); 3.80 (bs, 2H, NH$_2$); 5.15 (s, 2H, H-3+H-4-phenyl); 6.81 (m, 1H, H-5-phenyl); 6.90 (s, 1H, H-4-imidazole); 7.02 (m, 2H, H-6-phenyl+H-5-imidazole).

ESI(+)MS: m/z 204 (100, (M+H)$^+$).

By analogous procedure and by starting from 2-(2-nitrophenoxy)acetamide, 2-(2aminophenoxy)acetamide can be prepared.

m.p. 114–116° C.

$^1$H-NMR (400 MHz-DMSO-$d_6$) δ ppm: 4.30 (s, 2H, CH$_2$CO); 5.03 (s, 2H, NH$_2$); 6.45 (m, 1H, H-5); 6.61 (m, 1H, H-3); 6.67 (m, 1H, H-4); 6.72 (m, 1H, H-6); 7.45 (s, 1H, CONH); 7.73 (s, 1H, CONH$_2$).

ESI(+)MS: m/z 167 (100, (M+H)$^+$).

EXAMPLE 15

Preparation of 2-(imidazo[1,2-a]pyridin-2-ylmethyl)-1H-isoindole-1,3(2H)-dione 4 g (0.024 mol) of 2-(chloromethyl)imidazo[1,2-a]pyridine were dissolved in 140 ml of N,N-dimethylformamide and 4.81 g (0.026 mol) of potassium ftalimide were added portionwise. The mixture was heated at 60° C. for 20 hours. The precipitate was filtered, washed with water, diethylether and finally tetrahydrofuran, affording 4.8 g of the title compound.

m.p. 230–232° C.

$^1$H-NMR (400 MHz-DMSO-$d_6$) δ ppm: 4.88 (s, 2H, CH$_2$); 6.82 (m, 1H, H-6-imidazopyridine); 7.17 (m, 1H, H-5-imidazopyridine); 7.44 (m, 1H, H-7-imidazopyridine); 7.88 (m, 4H, H-phenyl); 8.42 (m, 1H, H-4-imidazopyridine).

ESI(+)MS: m/z 278 (100, (M+H)$^+$).

EXAMPLE 16

Preparation of imidazo[1,2-a]pyridin-2-ylmethanamine

A solution of 1.37 g (4.94 mmol) of 2-(imidazo[1,2-a]pyridin-2-ylmethyl)-1H-isoindole-1,3(2H)-dione in 14 ml of hydrazine hydrate 98% and 1 ml of ethanol. Was stirred at room temperature for an hour. The mixture was then poured into 25 ml of sodium hydroxide 35% and extracted with dichloromethane. The organic layer was dried over anhydrous sodium sulfate and evaporated to give 0.426 g of the title compound crystallized from diethylether.

m.p. 91–93° C.

$^1$H-NMR (400 MHz-DMSO-$d_6$) δ ppm: 1.98 (bs, 2H, $NH_2$); 3.78 (s, 2H, $CH_2$); 6.80 (m, 1H, H-5); 7.15 (m, 1H, H-6); 7.41 (m, 1H, H-7); 7.73 (s, 1H, H-3); 8.46 (m, 1H, H-4).

ESI(+)MS: m/z 148 (100, (M+H)$^+$).

EXAMPLE 17

Preparation of the Polymer Supported Compound (VIII)

A solution of 8.72 g (69.1 mmol) of 4-mercaptophenol in 20 ml of dry N,N-dimethylformamide was added dropwise to a solution of 7.76 g (69.1 mmol) of potassium t-butoxyde in 120 ml of the same solvent, under argon atmosphere, at 5° C., over a period of 20 minutes. 25 g (19.75 mmol) of the Merrifield resin (VII) (Novabiochem loading 0.79 mmol/g) was added to the solution and the temperature was kept to 60° C. The mixture was gently stirred at 60° C. for 18 hours and at 22° C. for 24 hours. The resin was then filtered, washed with N,N-dimethylformamide, dichloromethane, methanol and evaporated. The loading of 4-mercaptophenol on the resin was calculated from the percentage of sulfur determined via microanalysis: S 2.64%; loading 0.755 mmol S/g. The presence of OH group was confirmed via DRIFTS (broad strong band 3180–3520 nm).

EXAMPLE 18

Preparation of the Polymer Supported Compound (IX)

7.98 g (39.6 mmol) of 4-nitrophenylchloroformate and 4.35 ml (39.6 mmol) of N-methylmorpholine were added to 24 g (19.8 mmol) of the polymer supported compound (VIII) swelled in 200 ml of dichloromethane under argon atmosphere. The mixture was stirred at 22° C. for 22 hours. The obtained compound (IX) was filtered, washed with dichloromethane, methanol and evaporated under vacuum. The loading of 4-nitro-phenylchloroformate on the resin was calculated from the percentage of sulfur determined via microanalysis: S 2.34%; loading 0.731 mmol S/g. The disappearance of the OH band (broad strong band 3400 nm) and the appearance of carbonate group were monitored via DRIFTS (strong band 1785 nm).

EXAMPLE 19

Preparation of a Polymer Supported Compounds (X)

A solution of 2-amino-5-isopropyl-1,3-thiazole (39.6 mmol) in 12.5 ml of dichloromethane was added to the polymer supported compound (IX) (19.8 mmol) swelled in 200 ml of dichloromethane under argon atmosphere. The mixture was stirred at 22° C. for 22 hours. The obtained compound (X) was filtered, washed with dichloromethane, methanol and evaporated under vacuum. The loading of 2 amino-5-isopropyl-1,3-thiazole on the resin was calculated from the percentage of sulfur determined via microanalysis: S 4.21%; loading 0.724 mmol S/g. The presence of carbamate group was confirmed via DRIFTS (strong band 1742 nm).

EXAMPLE 20

Preparation via Parallel Synthesis of the Compounds of Formula (I)

The amines (V) (0.236 mmol) and N,N-diisopropylethylamine (0.236 mmol) were added to the polymer supported compounds (X) (0.118 mmol) swelled in 3 ml of toluene in the Argonaut Quest 210 apparatus vessels. 128 mg (4 eq) of N,N-diisopropylethylamine resin bounded (PS-DIEA loading 3.68 mmol/g) was used whenever the amines were in the salified form. The reactions were stirred for 22 hours at 60° C., then the reaction mixtures were filtered and the resin washed with dichloromethane. The liquid phase, recovered in Climax test tubes, was evaporated under nitrogen flux at 35° C. using Liebisch Termochem Metal-block thermostat. The obtained crude products were triturated with diethylether-dichloromethane and the resulting solids were filtered on frit equipped syringes (Alltech extract-clean filter tubes 1.5 ml, Alltech Teflon frits for 1.5 ml tubes). The products were finally dried under vacuum.

Employing this procedure and using the suitable amine the following compounds can be prepared:

N-(5-isopropyl-1,3-thiazol-2-yl)-4-morpholine carboxamide;

N-(5-isopropyl-1,3-thiazol-2-yl)-N'-(4-methylphenyl) urea;

N-(5-isopropyl-1,3-thiazol-2-yl)-N'-(3-fluorophenyl) urea;

N-(5-isopropyl-1,3-thiazol-2-yl)-N'-(4-cyanophenyl) urea;

N-(5-isopropyl-1,3-thiazol-2-yl)-N'-(3-cyanophenyl) urea;

N-(5-isopropyl-1,3-thiazol-2-yl)-N'-(2,6-dimethylphenyl)urea;

N-(5-isopropyl-1,3-thiazol-2-yl)-N'-(4-fluorobenzyl) urea;

N-(5-isopropyl-1,3-thiazol-2-yl)-N'-(3-acetylphenyl) urea;

$^1$H-NMR (400 MHz-DMSO-$d_6$) δ ppm: 1.24 (d, 6H, J=7.0, $CH_3CHCH_3$); 3.06 (m, 1H, $CH_3CHCH_3$); 2.55 (s, 3H, $COCH_3$); 7.32 (t, 1H, J=7.6, H-5'-phenyl); 7.44 (t, 1H, J=7.9, H-5'-phenyl); 7.5–7.8 (m, 2H, H-4', H-6'-phenyl); 8.08 (s, 1H, H-2'-phenyl); 7.04 (s, 1H, H-thiazole); 9.2 (bs, 1H, CON$\underline{H}$-phenyl); 10.5 (bs, 1H, N$\underline{H}$CONHPh);

N-(5-isopropyl-1,3-thiazol-2-yl)-N'-(4-acetylphenyl) urea;

3-({[(5-isopropyl-1,3-thiazol-2-yl)amino] carbonyl}amino)benzoic acid;

N-(5-isopropyl-1,3-thiazol-2-yl)-N'-(4-isopropylphenyl) urea;

3-({[(5-isopropyl-1,3-thiazol-2-yl)amino] carbonyl}amino)benzamide $^1$H-NMR (400 MHz-DMSO-$d_6$) δ ppm: 1.24 (d, 6H, J=6.8, $CH_3CHCH_3$); 3.05 (ept, 1H, J=6.8, $CH_3CHCH_3$); 7.32 (t, 1H, J=7.6, H-5'-phenyl); 7.35 (t, 1H, J=1.5, H-2'-phenyl); 7.49 (d, 1H, J=7.6, H-6'-phenyl); 7.62 (dd, 1H, J=7.6, 1.5, H-4'-phenyl); 7.04 (s, 1H, H-thiazole); 9.64 (s, 1H, CON$\underline{H}$-phenyl); 10.36 (s, 1H, N$\underline{H}$CONHPh);

N-(5-isopropyl-1,3-thiazol-2-yl)-N'-(4-methoxybenzyl) urea;

N-(5-isopropyl-1,3-thiazol-2-yl)-N'-(4-butylphenyl)urea;

N-(5-isopropyl-1,3-thiazol-2-yl)-N'-(4-trifluoromethylphenyl)urea;

N-(5-isopropyl-1,3-thiazol-2-yl)-N'-(3-bromophenyl) urea;

N-(5-isopropyl-1,3-thiazol-2-yl)-N'-(4-cyclohexyphenyl) urea;

N-(5-isopropyl-1,3-thiazol-2-yl)-N'-(4-phenoxyphenyl) urea $^1$H-NMR (400 MHz-DMSO-$d_6$) δ ppm: 1.24 (d, 6H, J=7.0, $CH_3CHCH_3$); 3.05 (m, 1H, $CH_3CHCH_3$); 6.96 (m, 4H, H-3', H-5'-phenyl, H-2', H-6'-phenyl); 7.02 (s, 1H, H-thiazole); 7.08 (m, 1H, H-4'-phenoxy); 7.35 (m, 2H, H-3', H-5'-phenoxy); 7.47 (m, 2H, H-2', H-6'-phenyl); 8.95 (bs, 1H, CON$\underline{H}$-phenyl); 10.3 (bs, 1H, N$\underline{H}$CONH);

N-(5-isopropyl-1,3-thiazol-2-yl)-N'-(4-benzyloxphenyl) urea;

N-(5-isopropyl-1,3-thiazol-2-yl)-N'-(3,5-dimethylphenyl)urea $^1$H-NMR (300 MHz-DMSO-d$_6$) δ ppm: 1.23 (d, 6H, J=6.8, C$\underline{H_3}$CHC$\underline{H_3}$); 3.05 (ept, 1H, J=6.8, CH$_3$C$\underline{H}$CH$_3$); 2.22 (s, 6H, 2C$\underline{H_3}$); 6.65–7.06 (m, 3H, H-phenyl); 7.02 (s, 1H, H-thiazole); 6.71 (s, 1H, H-phenyl); 6.72 (s, 1H, H-phenyl); 8.75 (bs, 1H, CON$\underline{H}$-phenyl); 10.3 (bs, 1H, N$\underline{H}$CONH).

ESI(+)–MS: m/z 362 (100,(M+H)$^+$);

N-(5-isopropyl-1,3-thiazol-2-yl)-N'-(2,3-dimethylphenyl)urea;

N-(5-isopropyl-1,3-thiazol-2-yl)-N'-(3-methoxy[1,1'-biphenyl]-4-yl)urea;

N-(5-isopropyl-1,3-thiazol-2-yl)-3,4-dihydro-2(1H)-isoquinoline carboxamide;

N-benzyl-N'-(5-isopropyl-1,3-thiazol-2-yl)-N-methylurea;

N-(5-isopropyl-1,3-thiazol-2-yl)-6,7-dimethoxy-3,4-dihydro-2(1H)-isoquinoline carboxamide $^1$H-NMR (400 MHz-DMSO-d$_6$) δ ppm: 1.21 (d, 6H, J=6.4, C$\underline{H_3}$CHC$\underline{H_3}$); 2.99 (ept, 1H, J=6.8, CH$_3$C$\underline{H}$CH$_3$); 2.7 (t 2H, J=5.5, CH$_2$NCH$_2$C$\underline{H_2}$); 3.68 (t, 2H, J=5,5, C$\underline{H_2}$NCH$_2$CH$_2$); 3.69 (s, 3H, OCH$_3$); 3.71 (s, 3H, OCH$_3$);4.55 (s, 2H, C$\underline{H_2}$NCH$_2$CH$_2$); 6.97 (s, 1H, H-thiazole); 6.71 (s, 1H, H-phenyl); 6.72 (s, 1H, H-phenyl); 10.7 (bs, 1H, NH).

ESI(+)–MS: m/z 362 (100, (M+H)$^+$).

N-(5-isopropyl-1,3-thiazol-2-yl)-N'-[(3-chloro-4-methyl)phenyl]urea;

N-(5-isopropyl-1,3-thiazol-2-yl)-N'-[(3-chloro-6-methyl)phenyl]urea;

N-(5-isopropyl-1,3-thiazol-2-yl)-N'-(2,5-dimethoxyphenyl)urea $^1$H-NMR (400 MHz-DMSO-d$_6$) δ ppm: 1.24 (d, 6H, J=7.0, C$\underline{H_3}$CHC$\underline{H_3}$); 3.07 (m, 1H, J=7.0, CH$_3$C$\underline{H}$CH$_3$); 3.68, 3.80 (two s 6H, 2-OC$\underline{H_3}$); 7.04 (d, J=1.0, 1H, H-thiazole); 6.53 (dd, 1H, J=3.0, 8.9, H-4'-phenyl); 6.93 (d, 1H, J=8.9, H-3'-phenyl); 7.79 (d, 1H, J=3.0, H-6'-phenyl); 8.7 (bs, 1H, N$\underline{H}$Ph); 10.9 (bs, 1H, N$\underline{H}$CONHPh);

N-(5-isopropyl-1,3-thiazol-2-yl)-N'-(3,4-dimethoxyphenyl)urea $^1$H-NMR (400 MHz-DMSO-d$_6$) δ ppm: 1.23 (d, 6H, J=7.0, C$\underline{H_3}$CHC$\underline{H_3}$); 3.05 (ept, 1H, J=7.0, CH$_3$C$\underline{H}$CH$_3$); 3.7 (s, 3H, OC$\underline{H_3}$); 3.73 (s, 3H, OC$\underline{H_3}$); 7.02 (s, 1H, H-thiazole); 6.8–7.2 (m, 3H, H-phenyl); 8.76 (s, 1H, NHCON$\underline{H}$Ph); 10.2 (s, 1H, N$\underline{H}$CONHPh);

N-(5-isopropyl-1,3-thiazol-2-yl)-N'-[(2-methoxy-5-chloro)phenyl]urea;

N-(5-isopropyl-1,3-thiazol-2-yl)-N'-((2-chloro-4-methoxyphenyl)urea;

N-(5-isopropyl-1,3-thiazol-2-yl)-N'-(3,5-dichlorophenyl)urea;

N-[(1,1'-biphenyl)-2-yl]-N'-(5-isopropyl-1,3-thiazol-2-yl)urea;

N-ethyl-N'-(5-isopropyl-1,3-thiazol-2-yl)-N-phenylurea;

N-[4-({[(5-isopropyl-1,3-thiazol-2-yl)amino]carbonyl}amino)-2-methoxyphenyl]acetamide;

2-({[(5-isopropyl-1,3-thiazol-2-yl)amino]carbonyl}amino)-N-phenylbenzamide;

N-(5-isopropyl-1,3-thiazol-2-yl)-N'-(2-morpholinophenyl)urea;

N-[4-({[(5-isopropyl-1,3-thiazol-2-yl)amino]carbonyl}amino)phenyl]-N-methyl acetamide $^1$H-NMR (400 MHz-DMSO-d$_6$) δ ppm: 1.22 (d, 6H, J=6.6, C$\underline{H_3}$CHC$\underline{H_3}$); 3.08 (m, 1H, CH$_3$C$\underline{H}$CH$_3$); 1.73 (s, 3H, NCOC$\underline{H_3}$); 7.03 (s, 1H, H-thiazole); 3.09 (s, 3H, C$\underline{H_3}$NCOCH$_3$); 7.23 (d, 2H, J=8.1, H-6', H-4'-phenyl); 7.51 (d, 2H, J=8.1, H-5', H-3'-phenyl); 9.1 (bs, 1H, NHCONH$\underline{H}$Ph); 10.4 (bs, 1H, N$\underline{H}$CONHPh);

N-(2-{[cyclohexyl(methyl)amino]methyl}phenyl)-N'-(5-isopropyl-1,3-thiazol-2-yl)urea;

N-[3-({[(5-isopropyl-1,3-thiazol-2-yl)amino]carbonyl}amino)-4-methoxyphenyl]acetamide;

N-(5-isopropyl-1,3-thiazol-2-yl)-4-(4-methoxyphenyl)-1-piperazine carboxamide;

N-(2-furylmethyl-N'-(5-isopropyl-1,3-thiazol-2-yl)urea $^1$H-NMR (400 MHz-DMSO-d$_6$) δ ppm: 1.24 (d, 6H, J=6.8, C$\underline{H_3}$CHC$\underline{H_3}$); 2.99 (ept, 1H, J=6.8, CH$_3$C$\underline{H}$CH$_3$); 4.32 (d, 2H, J=5.6, NHC$\underline{H_2}$); 6.26 (d, 1H, J=3, H-5'-furyl); 6.4 (d, 1H, J=3, H-4'-furyl); 6.98 (s, 1H, H-thiazole); 6.93 (t, 1H, N$\underline{H}$CH$_2$); 7.59 (s, 1H, H-3'-furyl); 10.19 (bs, 1H, NHCO).

ESI(+)–MS: m/z 266 (100, (M+H)$^+$);

N-(4-fluorophenyl)-N'-(5-isopropyl-1,3-thiazol-2-yl)urea;

N-(2-methoxybenzyl)-N'-(5-isopropyl-1,3-thiazol-2-yl)urea;

N-(5-isopropyl-1,3-thiazol-2-yl)-N'-[2-(1-methyl-1H-pyrrol-2-yl)ethyl]urea;

N-(3,4-dimethoxybenzyl)-N'-(5-isopropyl-1,3-thiazol-2-yl)urea $^1$H-NMR (400 MHz-DMSO-d$_6$) δ ppm: 1.21 (d, 6H, J=7.0, C$\underline{H_3}$CHC$\underline{H_3}$); 3.01 (ept, 1H, J=7.0, CH$_3$C$\underline{H}$CH$_3$); 3.69 (s, 3H, OCH$_3$); 3.72 (s, 3H, OCH$_3$); 4.22 (d, 2H, J=5.0, NHC$\underline{H_2}$Ph); 6.8–6.9 (m, 3H, H-phenyl); 6.96 (s, 1H, H-thiazole);

N-(5-isopropyl-1,3-thiazol-2-yl)-4-oxo-1-phenyl-1,3,8-triazaspiro[4.5]decane-8-carboxamide $^1$H-NMR (400 MHz-DMSO-d$_6$) δ ppm: 1.23 (d, 6H, J=6.8, C$\underline{H_3}$CHC$\underline{H_3}$); 3.03 (ept, 1H, J=6.8, CH$_3$C$\underline{H}$CH$_3$); 1.62 (d, 2H, J=13.6, H-3'eq, H-5'eq-piperidine); 2.4 (td, 2H, J=13.6, 5.1, H-3'ax, H-5'ax-piperidine); 3.46 (bt, 2H, J=10.4, H-6'ax, H-2'ax-piperidine); 4.14 (bd, 2H, J=10.4, H-6'eq, H-2'eq-piperidine); 4.58 (s, 2H, CONHC$\underline{H_2}$NPh); 6.6–6.7 (m, 3H, H-2', H-6', H-4'-phenyl); 7.14 (t, 2H, J=7.5, H-3', H-5'-phenyl); 6.98 (bs, 1H, H-thiazole); 8.75 (bs, 1H, CONHCH$_2$NPh); 10.85 (bs, 1H, thiazole-N$\underline{H}$CON);

N-(5-isopropyl-1,3-thiazol-2-yl)-1,4-dioxa-8-azaspiro[4.5]decane-8-carboxamide;

N-(5-isopropyl-1,3-thiazol-2-yl)-N'-[2-(1-piperidinyl)ethyl]urea;

N-(5-isopropyl-1,3-thiazol-2-yl)-N'-[2-(1-morpholinyl)ethyl]urea;

4-(4-fluorophenyl)-N-(5-isopropyl-1,3-thiazol-2-yl)-1-piperazine carboxamide;

N-[4-(4-chlorophenyl)-3-ethyl-5-isoxazolyl]-N'-(5-isopropyl-1,3-thiazol-2-yl)urea;

N-[(4-fluorophenyl)(hydroxy)methyl]-N-(5-isopropyl-1,3-thiazol-2-yl)-1-piperidine carboxamide;

N-(3-ethynylphenyl)-N'-(5-isopropyl-1,3-thiazol-2-yl)urea;

N-(2-methoxy-3-fluorophenyl)-N'-(5-isopropyl-1,3-thiazol-2-yl)urea;

N-(5-isopropyl-1,3-thiazol-2-yl)-N'-(4-oxo-1-piperidinyl)urea;

N-(3-acetylaminophenyl)-N'-(5-isopropyl-1,3-thiazol-2-yl)urea;

N-[3-(2-furyl)-1H-pyrazol-5yl]-N'-(5-isopropyl-1,3-thiazol-2-yl)urea;

N-{4-[ethyl(isopropyl)amino]phenyl}-N'-(5-isopropyl-1,3-thiazol-2-yl)urea;

N-(1,3-benzodioxol-5-yl)-N'-(5-isopropyl-1,3-thiazol-2-yl)urea;

5-({[(5-isopropyl-1,3-thiazol-2-yl)amino]carbonyl}amino)-1-phenyl-1H-pyrazole-4-carboxamide;

N-(5-isopropyl-1,3-thiazol-2-yl)-N'-(4-pyridinylmethyl)urea;

N-(5-isopropyl-1,3-thiazol-2-yl)-N'-(2-pyrazinyl)urea;

n-(5-isopropyl-1,3-thiazol-2-yl)-N'-(5-phenyl-1,3,4-oxadiazol-2-yl)urea;

N-(5-isopropyl-1,3-thiazol-2-yl)-4-(2-oxo-2,3-dihydro-1H-benzimidazol-1-yl)-1-piperidine carboxamide $^1$H-NMR (400 MHz-DMSO-$d_6$) δ ppm: 1.23 (d, 6H, J=7.0, C$\underline{H}_3$CHC$\underline{H}_3$); 3.01 (ept, 1H, J=7.0, CH$_3$C$\underline{H}$CH$_3$); 1.69 (bd, 2H, J=9.8, H-3'eq,H-5'eq-piperidine); 2.21 (m, 2H, H-3'ax, H-5'ax-piperidine); 3.46 (bt, 2H, J=12.4, H-2'ax, H-6'ax-piperidine); 4.14 (m, 3H, H-2'eq, H-6'eq, H-4'ax-piperidine); & .9–7.2 (m, 4H, aromatics); 6.98 (s, 1H, H-thiazole); 10.8 (bs, 2H, N$\underline{H}$CON$\underline{H}$);

N-(1,3-benzothiazol-6-yl)-N'-(5-isopropyl-1,3-thiazol-2-yl)urea;

$^1$H-NMR (400 MHz-DMSO-$d_6$) δ ppm: 1.24 (d, 6H, J=6.8, C$\underline{H}_3$CHC$\underline{H}_3$); 3.05 (ept, 1H, J=6.8, CH$_3$C$\underline{H}$CH$_3$); 7.5 (dd, 1H, J=8.8, 1.9, H-5'-benzothiazole); 7.98 (d, 1H, J=8.8, H-4'-benzothiazole); 8.38 (d, 1H, J=1.9, H-7'-benzothiazole); 9.22 (s, 2H, H-2'-benzothiazole+NHCONHPh); 7.04 (s, 1H, H-thiazole); 10.41 (s, 1H, N$\underline{H}$CONHPh);

N-(1,3-dimethyl-1H-pyrazol-5-yl)-N'-(5-isopropyl-1,3-thiazol-2-yl)urea;

N-(3-phenyl-1-methyl-1H-pyrazol-5yl)-N'-(5-isopropyl-1,3-thiazol-2-yl)urea;

N-(5-isopropyl-1,3-thiazol-2-yl)-3-hydroxy-1-piperidine carboxamide;

N-(5-isopropyl-1,3-thiazol-2-yl)-N'-(2-methyl-1,3-dioxo-2,3-dihydro-1H-isoindol-5-yl)urea;

N-(5-isopropyl-1,3-thiazol-2-yl)-4-benzyl-1-piperazine carboxamide;

N-(5-isopropyl-1,3-thiazol-2-yl)-4-methyl-1-piperazine carboxamide;

4-hydroxy-N-(5-isopropyl-1,3-thiazol-2-yl)-1-piperidine carboxamide;

N-(5-isopropyl-1,3-thiazol-2-yl)-3-azabicyclo[3.2.2]nonane-3-carboxamide;

N-(5-isopropyl-1,3-thiazol-2-yl)-4-(4-acetylphenyl)-1-piperazine carboxamide;

$^1$H-NMR (400 MHz-DMSO-$d_6$) δ ppm: 1.21 (d, 6H, J=7.0, C$\underline{H}_3$CHC$\underline{H}_3$); 2.99 (ept, 1H, J=7.0, CH$_3$C$\underline{H}$CH$_3$); 2.44 (s, 3H, C$\underline{H}_3$COPh); 3.29 (bt, 4H, CH$_2$-2', 6'-piperazine); 3.63 (bt, 4H, CH$_2$-3', 5'-piperazine); 6.97 (d, 2H, J=9.2, H-3', 5'-phenyl); 7.8 (d, 2H, J=9.2, H-2', 6'-phenyl); 6.97 (s, 1H, H-thiazole); 10.95 (bs, 1H, N$\underline{H}$CON);

4-[bis(4-fluorophenyl)-N-(5-isopropyl-1,3-thiazol-2-yl)-1-piperazine carboxamide;

N-(5-isopropyl-1,3-thiazol-2-yl)-4-oxo-2,3,4,5-tetrahydro-1H-1,5-benzodiazepine-1-carboxamide;

N-(5-isopropyl-1,3-thiazol-2-yl)-N'-(5,6,7,8-tetrahydro-1-naphtalenyl)urea;

N-(4-phenyl-2-thiazolyl)-N'-(5-isopropyl-1,3-thiazol-2-yl)urea;

4-(4-fluorobenzoyl)-N-(5-isopropyl-1,3-thiazol-2-yl)-1-piperidine carboxamide;

N-(5-isopropyl-1,3-thiazol-2-yl)-N'-1,3-dihydro-2-benzofuran-5-yl)urea;

N-(5-isopropyl-1,3-thiazol-2-yl)-N'-(2-pyrimidinyl)-1-piperazine carboxamide;

N-(5-isopropyl-1,3-thiazol-2-yl)-3-oxo-3,4-dihydro-1(2H)-quinoxaline;

N-(5-isopropyl-1,3-thiazol-2-yl)-N'-(1H-indazol-6-yl)urea $^1$H-NMR (500 MHz-DMSO-$d_6$) δ ppm: 1.25 (d, 6H, J=6.8, C$\underline{H}_3$CHC$\underline{H}_3$); 3.07 (m, 1H, CH$_3$C$\underline{H}$CH$_3$); 6.94 (d, 1H, J=8.4, H-5'-indazole); 7.65 (d, 1H, J=8.4, H-4'-indazole); 7.94 (m, 2H, H-3', H-7'-indazole); 7.04 (s, 1H, H-thiazole); 9.12 (bs, 1H, CONH-indazole); 10.30 (bs, 1H, NH-thiazole); 12.87 (bs, 1H, NH-indazole).

ESI(+)–MS: m/z 302 (100, (M+H)$^+$);

N-(5-isopropyl-1,3-thiazol-2-yl)-N'-(2-chlorobenzyl)urea $^1$H-NMR (500 MHz-DMSO-$d_6$) δ ppm: 1.21 (d, 6H, J=6.9, C$\underline{H}_3$CHC$\underline{H}_3$); 3.03 (m, 1H, CH$_3$C$\underline{H}$CH$_3$); 4.38 (d, 2H, J=5.9, C$\underline{H}_2$); 7.3–7.44 (m, 4H, phenyl); 6.97 (d, 1H, J=0.9, H-thiazole); 7.10 (bs, 1H, N$\underline{H}$CH$_2$); 10.32 (bs, 1H, NH-thiazole).

ESI(+)–MS: m/z 310 (100, (M+H)$^+$);

N-(5-isopropyl-1,3-thiazol-2-yl)-N'-(2,4-dichlorobenzyl)urea;

N-(5-isopropyl-1,3-thiazol-2-yl)-N'-(3-fluorobenzyl)urea $^1$H-NMR (500 MHz-DMSO-$d_6$) δ ppm: 1.21 (d, 6H, J=6.8, C$\underline{H}_3$CHC$\underline{H}_3$); 3.03 (m, 1H, CH$_3$C$\underline{H}$CH$_3$); 4.32 (d, 2H, J=6.1, CH$_2$); 6.97 (d, 1H, J=0.9, H-thiazole); 7.04–7.4 (m, 5H, phenyl+N$\underline{H}$CH$_2$); 10.30 (bs, 1H, NH-thiazole).

ESI(+)–MS: m/z 294 (100, (M+H)$^+$);

N-(5-isopropyl-1,3-thiazol-2-yl)-N'-(3,4-dichlorobenzyl)urea $^1$H-NMR (500 MHz-DMSO-$d_6$) δ ppm: 1.21 (d, 6H, J=6.7, C$\underline{H}_3$CHC$\underline{H}_3$); 3.03 (m, 1H, CH$_3$C$\underline{H}$CH$_3$); 4.30 (d, 2H, J=6.1, C$\underline{H}_2$); 7.28 (dd, 1H, J=2.0, 8.2, H-6'-phenyl); 7.52 (d, 1H, J=2.0, H-2'-phenyl); 7.58 (d, 1H, J=8.2, H-5'-phenyl); 6.97 (d, 1H, J=0.9, H-thiazole); 7.12 (bs, 1H, N$\underline{H}$CH$_2$); 10.41 (bs, 1H, NH-thiazole).

ESI(+)–MS: m/z 143 (100, isopropylaminothiazole+H)$^+$); m/z 344 (65, (M+H)$^+$);

N-(5-isopropyl-1,3-thiazol-2-yl)-N'-(2,4-difluorobenzyl)urea $^1$H-NMR (300 MHz-DMSO-$d_6$) δ ppm: 1.21 (d, 6H, J=6.7 C$\underline{H}_3$CHC$\underline{H}_3$); 3.03 (m, 1H, CH$_3$C$\underline{H}$CH$_3$); 4.30 (d, 2H, J=6.0, C$\underline{H}_2$); 6.97 (d, 1H, J=0.9, H-thiazole); 7.0–7.4 (m, 4H, phenyl+N$\underline{H}$CH$_2$); 10.20 (bs, 1H, NH-thiazole).

ESI(+)–MS: m/z 312 (100, (M+H)$^+$);

N-(5-isopropyl-1,3-thiazol-2-yl)-N'-(2,5-difluorobenzyl)urea $^1$H-NMR (500 MHz-DMSO-$d_6$) δ ppm: 1.21 (d, 6H, J=6.9 C$\underline{H}_3$CHC$\underline{H}_3$); 3.02 (m, 1H, CH$_3$C$\underline{H}$CH$_3$); 4.35 (d, 2H, J=5.8, C$\underline{H}_2$); 7.08 (m, 2H, H-3', H-5'-phenyl); 7.39 (m, 1H, H-4'-phenyl); 6.95 (d, 1H, J=0.9, H-thiazole); 7.04 (bs, 1H, N$\underline{H}$CH$_2$); 10.08 (bs, 1H, NH-thiazole).

ESI(+)–MS: m/z 312 (100, (M+H)$^+$);

N-(5-isopropyl-1,3-thiazol-2-yl)-N'-2,6-difluorobenzyl)urea;

N-(5-isopropyl-1,3-thiazol-2-yl)-N'-[(4-hydroxy-3-methoxy)benzyl]urea;

N-(5-isopropyl-1,3-thiazol-2-yl)-N'-(5-methyl-2-furyl)urea $^1$H-NMR (500 MHz-DMSO-$d_6$) δ ppm: 1.21 (d, 6H, J=6.8, C$\underline{H}_3$CHC$\underline{H}_3$); 3.03 (m, 1H, CH$_3$C$\underline{H}$CH$_3$); 2.21 (s, 3H, CH$_3$); 4.23 (d, 2H, J=5.8, CH$_2$); 5.97, 6.11 (2s, 2H, furane); 6.96 (d, 1H, J=1.0, H-thiazole); 6.91 (bs, 1H, N$\underline{H}$CH$_2$); 10.14 (bs, 1H, NH-thiazole).

ESI(+)–MS: m/z 280 (100, (M+H)⁺);

N-(5-isopropyl-1,3-thiazol-2-yl)-N'-(4-methylsulfonylbenzyl)urea;

N-[(1R, 2R)-2-hydroxy-2,3-dihydro-1H-inden-1-yl]-N'-(5-isopropyl-1,3-thiazol-2-yl)urea;

N-(5-isopropyl-1,3-thiazol-2-yl)-N'-(4-chlorobenzyl)urea

¹H-NMR (500 MHz-DMSO-d₆) δ ppm: 1.21 (d, 6H, J=6.8, C$\underline{H}_3$CHC$\underline{H}_3$); 3.03 (m, 1H, CH₃C$\underline{H}$CH₃); 4.29 (d, 2H, J=6.1, C$\underline{H}_2$); 7.3, 7.37 (2d, 4H, J=8.5, phenyl); 6.97 (d, 1H, J=0.9, H-thiazole); 7.06 (bs, 1H, N$\underline{H}$CH₂); 10.30 (bs, 1H, NH-thiazole).

ESI(+)–MS: m/z 310 (100, (M+H)⁺);

N-(5-isopropyl-1,3-thiazol-2-yl)-N'-(2-pyridinylmethyl)urea

N-(5-isopropyl-1,3-thiazol-2-yl)-N'-(3,5-dimethoxybenzyl)urea;

¹H-NMR (500 MHz-DMSO-d₆) δ ppm: 1.21 (d, 6H, J=6.8, C$\underline{H}_3$CHC$\underline{H}_3$); 3.03 (m, 1H, CH₃C$\underline{H}$CH₃); 4.24 (d, 2H, J=5.9, C$\underline{H}_2$); 3.71 (s, 6H, 2 OCH₃); 6.37 (s, 1H, H-4'-phenyl); 6.44 (s, 2H, H-2', H-6'-phenyl); 6.97 (s, 1H, H-thiazole); 6.99 (bs, 1H, N$\underline{H}$CH₂); 10.22 (bs, 1H, NH-thiazole).

ESI(+)–MS: m/z 336 (100, (M+H)⁺);

N-(5-isopropyl-1,3-thiazol-2-yl)-N'-(3-pyridinylmethyl)urea;

N-(5-isopropyl-1,3-thiazol-2-yl)-N'-(4-trifluorobenzyl)urea;

N-(5-isopropyl-1,3-thiazol-2-yl)-N'-(3,4,5-trimethoxybenzyl)urea

¹H-NMR (300 MHz-DMSO-d₆) δ ppm: 1.21 (d, 6H, J=6.8, C$\underline{H}_3$CHC$\underline{H}_3$); 3.03 (m, 1H, CH₃C$\underline{H}$CH₃); 4.24 (d, 2H, J=5.9, C$\underline{H}_2$); 3.60, 3.65 (3s, 9H, 3 OCH₃); 6.60 (s, 2H, phenyl); 6.97 (s, 1H, H-thiazole); 6.99 (bs, 1H, N$\underline{H}$CH₂); 10.20 (bs, 1H, NH-thiazole).

ESI(+)–MS: m/z 366 (100, (M+H)⁺); m/z 181 (100, (CH₃O)₃—C₇H₄⁺);

N-(5-isopropyl-1,3-thiazol-2-yl)-N'-(2,4-dimethoxybenzyl)urea

¹H-NMR (300 MHz-DMSO-d₆) δ ppm: 1.21 (d, 6H, J=6.8, C$\underline{H}_3$CHC$\underline{H}_3$); 3.03 (m, 1H, CH₃C$\underline{H}$CH₃); 4.24 (d, 2H, J=5.9, C$\underline{H}_2$); 3.70, 3.78 (2s, 6H, 2 OCH₃); 6.48 (dd, 1H, H-5'-phenyl); 6.52 (d, 1H, H-3'-phenyl); 7.05 (d, 1H, H-6'-phenyl); 6.97 (s, 1H, H-thiazole); 6.80 (bs, 1H, N$\underline{H}$CH₂); 10.10 (bs, 1H, NH-thiazole).

ESI(+)–MS: m/z 336 (100, (M+H)⁺);

N-(5-isopropyl-1,3-thiazol-2-yl)-N'-(4-dimethylaminobenzyl)urea;

N-(5-isopropyl-1,3-thiazol-2-yl)-N'-(2,5-dimethoxybenzyl)urea;

N-(5-isopropyl-1,3-thiazol-2-yl)-N'-[(2-chloro-6-phenoxy)benzyl]urea;

N-(5-isopropyl-1,3-thiazol-2-yl)-N'-[(1R, 2S)-2-hydroxy-2,3-dihydro-1H-inden-1-yl]urea;

N-(5-isopropyl-1,3-thiazol-2-yl)-N'-[(3-hydroxy-4-methyl)phenyl]urea;

N-(5-isopropyl-1,3-thiazol-2-yl)-N'-[4-(1H-benzimidazol-2-yl)phenyl]urea;

N-(5-isopropyl-1,3-thiazol-2-yl)-N'-(3-phenyl-1H-pyrazol-5-yl)urea;

N-(5-isopropyl-1,3-thiazol-2-yl)-N'-(2-methyl-6-quinolinyl)urea

¹H-NMR (500 MHz-DMSO-d₆) δ ppm: 1.25 (d, 6H, J=6.8, C$\underline{H}_3$CHC$\underline{H}_3$); 3.07 (m, 1H, CH₃C$\underline{H}$CH₃); 2.61 (s, 3H, CH₃); 7.05 (s, 1H, H-thiazole); 7.36 (d, 1H, J=8.4, H-3'-quinoline); 7.65 (dd, 1H, J=2.0, 9.0, H-7'-quinoline); 7.85 (d, 1H, J=9.0, H-8'-quinoline); 8.14 (m, 2H, H-4', H-5'-quinoline); 9.22 (bs, 1H, NHCON$\underline{H}$-quinoline); 10.40 (bs, 1H, N$\underline{H}$-thiazole).

ESI(+)–MS: m/z 185 (100, (MH—(CH₃)₂—CH-aminothiazole)⁺); 327 (75, (M+H)⁺);

N-(5-isopropyl-1,3-thiazol-2-yl)-N'-[4-(cynanomethyl)phenyl]urea

¹H-NMR (500 MHz-DMSO-d₆) δ ppm: 1.24 (d, 6H, J=6.9, C$\underline{H}_3$CHC$\underline{H}_3$); 3.05 (m, 1H, CH₃C$\underline{H}$CH₃); 7.03 (s, 1H, H-thiazole); 3.94 (s, 2H, CH₂); 7.27 (d, 2H, H-3', H-5'-phenyl); 7.48 (d, 2H, J=8.5, H-2', H-6'-phenyl); 9.01 (bs, 1H, NH-phenyl); 10.30 (bs, 1H, NH-thiazole).

ESI(+)MS: m/z 301 (100, (M+H)⁺);

N-(5-isopropyl-1,3-thiazol-2-yl)-N'-(2-quinolinyl)urea

¹H-NMR (500 MHz-DMSO-d₆) δ ppm: 1.27 (d, 6H, J=6.8, C$\underline{H}_3$CHC$\underline{H}_3$); 3.13 (m, 1H, CH₃C$\underline{H}$CH₃); 7.17 (s, 1H, H-thiazole); 7.44 (m, 1H, H-3'-quinoline); 7.50 (m, 1H, H-6'-quinoline); 7.75 (m, 1H, H-7'-quinoline); 7.82 (m, 1H, H-8'-quinoline); 7.90 (m, 1H, H-5'-quinoline); 8.34 (m, 1H, H-4'-quinoline); 10.45 (bs, 1H, NHCON$\underline{H}$-quinoline); 13.02 (bs, 1H, N$\underline{H}$CON).

ESI(+)MS: m/z 313 (100, (M+H)⁺).

N-(5-isopropyl-1,3-thiazol-2-yl)-N'-(1-oxo-2,3-dihydro-1H-inden-5-yl)urea;

N-(5-isopropyl-1,3-thiazol-2-yl)-N'-(3-oxo-1,3-dihydro-2-benzofuran-5-yl)urea

¹H-NMR (500 MHz-DMSO-d₆) δ ppm: 1.24 (d, 6H, J=6.8, C$\underline{H}_3$CHC$\underline{H}_3$); 3.06 (m, 1H, CH₃C$\underline{H}$CH₃); 7.04 (s, 1H, H-thiazole); 5.35 (s, 1H, CH₂); 7.58 (d, 1H, J=8.4, H-5'-phenyl); 7.71 (d, 1H, J=8.4, H-6'-phenyl); 8.08 (s, 1H, H-2'-phenyl); 9.34 (bs, 1NHCONHPh); 10.50 (bs, 1H, N$\underline{H}$CON).

ESI(+)MS: m/z 318 (100, (M+H)⁺).

N-(5-isopropyl-1,3-thiazol-2-yl)-N'-(5-oxo-5,6,7,8-tetrahydro-2-naptalenyl)urea;

methyl-3-({[(5-isopropyl-1,3-thiazol-2-yl)amino]carbonyl}amino)-4-methylbenzoate ¹H-NMR (300 MHz-DMSO-d₆) δ ppm: 1.25 (d, 6H, J=6.8, C$\underline{H}_3$CHC$\underline{H}_3$); 3.10 (m, 1H, CH₃C$\underline{H}$CH₃); 2.30 (s, 3H, CH₃-phenyl); 3.80 (s, 3H, CH₃O); 7.05 (s, 1H, H-thiazole); 7.30 (d, 1H, H-5'-phenyl); 7.58 (dd, 1H, H-6'-phenyl); 8.55 (m, 2H, H-2'-phenyl+N$\underline{H}$Ph); 10.80 (bs, 1H, N$\underline{H}$-thiazole).

ESI(+) MS: m/z 334 (100, (M+H)⁺);

methyl-4-({[(5-isopropyl-1,3-thiazol-2-yl)amino]carbonyl}amino)-3-methylbenzoate ¹H-NMR (300 MHz-DMSO-d₆) δ ppm: 1.21 (d, 6H, C$\underline{H}_3$CHC$\underline{H}_3$); 3.03 (m, 1H, CH₃C$\underline{H}$CH₃); 2.25 (s, 3H, CH₃-phenyl); 3.83 (s, 3H, CH₃O); 7.03 (s, 1H, H-thiazole); 7.30 (d, 1H, H-3'-phenyl); 7.53 (dd, 1H, H-4'-phenyl); 8.50 (m, 2H, H-6'-phenyl+N$\underline{H}$Ph); 10.70 (bs, 1H, N$\underline{H}$-thiazole).

ESI(+)MS: m/z 334 (100, (M+H)⁺);

N-(5-isopropyl-1,3-thiazol-2-yl)-N'-(4-imidazo[1,2-a]pyridin-2-yl-phenyl)urea

¹H-NMR (300 MHz-DMSO-d₆) δ ppm: 1.21 (d, 6H, J=6.8, C$\underline{H}_3$CHC$\underline{H}_3$); 3.03 (m, 1H, CH₃C$\underline{H}$CH₃); 7.03 (s, 1H, H-thiazole); 6.84, 7.20 (2m, 2H, H-5', H-6"-imidazopyridine); 7.50, 7.90 (2m, 5H, H-2', H-3', H-5', H-6'-phenyl+H-7'-imidazopyridine); 8.30 (s, 1H, H-3'-imidazopyridine); 8.50 (d, 1H, H-4'-imidazopyridine); 9.00 (bs, 1H, NHCONHPh); 10.30 (bs, 1H, N$\underline{H}$CON).

ESI(+)MS: m/z 236 (100, (MH—(CH₃)₂—CH-aminothiazole)⁺); m/z 378 (85, (M+H)⁺);

ethyl-4-({[(5-isopropyl-1,3-thiazol-2-yl)amino]carbonyl}amino)benzoate

¹H-NMR (300 MHz-DMSO-d₆) δ ppm: 1.20 (d, 6H, C$\underline{H}_3$CHC$\underline{H}_3$); 3.03 (m, 1H, CH₃C$\underline{H}$CH₃); 7.00 (s, 1H, H-thiazole); 1.15 (t, 3H, CH₃); 3.58 (s, 2H, CH₂-phenyl); 4.06 (q, 2H, CH₂O); 7.16, 7.38 (2d, 4H, phenyl); 8.90 (bs, 1H, NHCON$\underline{H}$Ph); 10.30 (bs, 1H, N$\underline{H}$CON).

ESI(+)MS: m/z 348 (100, (M+H)+);

(2R)-1-benzyl-2-({[(5-isopropyl-1,3-thiazol-2-yl)amino]carbonyl}amino)propanamide;

2-hydroxy-5-({[(5-isopropyl-1,3-thiazol-2-yl)amino]carbonyl}benzoic acid 2-chloro-5-({[(5-isopropyl-1,3-thiazol-2-yl)amino]carbonyl}amino)benzoic acid;

$^1$H-NMR (400 MHz-DMSO-d$_6$) δ ppm: 1.24 (d, 6H, J=6.8, CH$_3$CHCH$_3$); 3.04 (m, 1H, CH$_3$CHCH$_3$); 7.02 (s, 1H, H-thiazole); 7.35 (d, 1H, J=8.8, H-5'-phenyl); 7.55 (dd, 1H, H-6'-phenyl); 7.88 (bs, 1H, H-2'-phenyl); 9.75 (bs, 1H, NHCONHPh); 11.00 (bs, 1H, NHCON).

ESI(+)MS: m/z 340 (100, (M+H)+);

3-({[(5-isopropyl-1,3-thiazol-2-yl)amino]carbonyl}amino)benzoic acid $^1$H-NMR (500 MHz-DMSO-d$_6$) δ ppm: 1.24 (d, 6H, J=6.8, CH$_3$CHCH$_3$); 3.03 (m, 1H, CH$_3$CHCH$_3$); 7.04 (s, 1H, H-thiazole); 7.40 (dd, 1H, J=7.9, H-5'-phenyl); 7.58, 7.63 (2d, 2H, J=7.9, H-4', H-6'-phenyl); 8.13 (s, 1H, H-2'-phenyl); 9.28 (s, 1H, NHCONHPh); 10.50 (bs, 1H, NHCON).

ESI(+)MS: m/z 306 (100, (M+H)+);

N-(5-isopropyl-1,3-thiazol-2-yl)-N'-(5-methyl-3-isoxazolyl)urea;

N-(5-isopropyl-1,3-thiazol-2-yl)-N'-(2,6-dimethoxyphenyl)urea;

N-(5-isopropyl-1,3-thiazol-2-yl)-N'-(2,3-dimethoxybenzyl)urea $^1$H-NMR (300 MHz-DMSO-d$_6$) δ ppm: 1.21 (d, 6H, J=6.8, CH$_3$CHCH$_3$); 3.03 (m, 1H, CH$_3$CHCH$_3$); 4.32 (d, 2H, J=6.1, CH$_2$); 3.72, 3.75 (2s, 6H, 2 OCH$_3$); 6.8–7.0 (m, 3H, phenyl); 6.97 (s, 1H, H-thiazole); 6.90 (bs, 1H, NHCH$_2$); 10.20 (bs, 1H, NH-thiazole).

ESI(+)–MS: m/z 336 (100, (M+H)+);

N-(5-isopropyl-1,3-thiazol-2-yl)-N'-(3,4-difluorobenzyl)urea;

N-(5-isopropyl-1,3-thiazol-2-yl)-N'-(2,4-dimethylphenyl)urea;

N-(5-isopropyl-1,3-thiazol-2-yl)-N'-butylurea $^1$H-NMR (300 MHz-DMSO-d$_6$) δ ppm: 1.20 (d, 6H, CH$_3$CHCH$_3$); 3.00 (m, 1H, CH$_3$CHCH$_3$); 0.85 (t, 3H, CH$_3$); 1.20–1.40 (m, 4H, CH$_2$—CH$_2$); 3.10 (m, 2H, CH$_2$—NH); 6.94 (d, 1H, J=1.0, H-thiazole); 6.49 (t, 1H, NHCH$_2$); 10.5 (bs, 1H, NH-thiazole).

ESI(+)–MS: m/z 242 (100, (M+H)+);

N-(5-isopropyl-1,3-thiazol-2-yl)-N'-benzoylurea;

N-(5-methyl-1,3-thiazol-2-yl)-N'-(2,6-dimethylphenyl)urea;

N-(5-methyl-1,3-thiazol-2-yl)-N'-benzylurea;

N-(5-methyl-1,3-thiazol-2-yl)-N'-butylurea;

N-(5-methyl-1,3-thiazol-2-yl)-4-morpholinecarboxamide;

N-(5-methyl-1,3-thiazol-2-yl)-N'-phenylurea;

N-(5-methyl-1,3-thiazol-2-yl)N'-(4-methoxybenzylurea;

N-(5-methyl-1,3-thiazol-2-yl)-N'-(4-fluorophenyl)urea;

N-[(1-ethyl-2-pyrrolidinyl)methyl]-N'-(5-methyl-1,3-thiazol-2-yl)urea;

N-(5-methyl-1,3-thiazol-2-yl)-N'-(5-hydroxy-1H-pyrazol-3-yl)urea;

N-(5-methyl-1,3-thiazol-2-yl)-N'-(3-pyridinyl)urea;

N-(4-fluorophenyl)-N'-(5-methyl-1,3-thiazol-2-yl)urea.

All compounds were characterized by mass spectrometry (MS). LC-MS confirmed that in each case the principle component had a molecular ion corresponding to the expected product. The compounds showed an HPLC area % ranging from 70 to 100. HPLC Analysis:

Instrument: Beckman System Gold Cromatographer (127 Solvent module, 168 Detector, 507e Autosampler)

Mobile A: H$_2$O/CH$_3$CN (90/10)+0.1% TFA.

Mobile B: H$_2$O/CH$_3$CN (10/90)+0.075% TFA.

Flow rate: 1.5 ml/mm.

Sample volume: 20 cml.

Column: Supelco™, Discovery RP Amide C16, 5 μm. (50×4.6)mm

Temp: 25° C.

Gradient:

| Time (min) | % A | % B |
|---|---|---|
| 0 | 0 | 100 |
| 6.5 | 0 | 100 |
| 7 | 100 | 0 |
| 10 | 100 | 0 |

Detection: diode array UV 254 nm.

All the compounds were analyzed by MS spectrometry (ESI) using a LCQ Finnigan Mass Spectrometer. 37 randomly chosen compounds were analyzed by H$^1$-NMR. The spectra were run on a Varian XL 400 Spectrometer.

What is claimed is:

1. A 2-amino-1,3-thiazole derivative of formula (I)

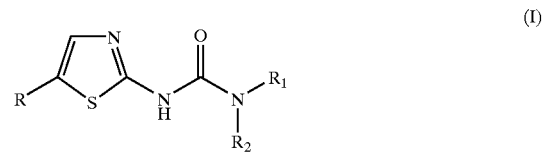

(I)

wherein

R is bromine, chlorine, a straight or branched C$_1$–C$_4$ alkyl group, a phenyl group, a cycloalkyl group; R$_2$ is hydrogen and R$_1$ is an optionally substituted aryl or an arylalkyl or heterocyclyl-alkyl group having from 1 to 4 carbon atoms within the alkyl chain, wherein R$_1$ is not 4-(5-oxazolyl) phenyl.

2. A 2-amino-1,3-thiazole derivative of formula (I)

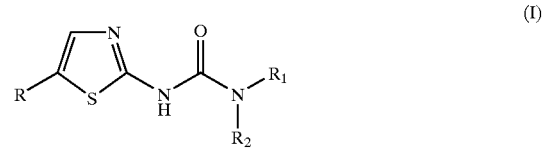

(I)

wherein

R is a straight or branched C$_1$–C$_6$ alkyl group and, together with the nitrogen atom to which they are bonded, R$_1$ and R$_2$ form a substituted or unsubstituted, optionally benzocondensed or bridged 5 to 7 membered heterocycle, or a 9 to 11 membered spiro-heterocycle.

3. A 2-amino-1,3-thiazole derivative of formula (I)

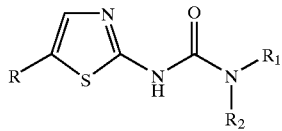

(I)

wherein

R is a straight or branched $C_1$–$C_6$ alkyl group; $R_2$ is a straight or branched $C_1$–$C_4$ alkyl or $C_2$–$C_4$ alkenyl or alkynyl group and $R_1$ is an aryl or arylalkyl group with from 1 to 4 carbon atoms within the straight or branched alkyl chain.

* * * * *